(12) United States Patent
Tsuda

(10) Patent No.: US 9,146,095 B2
(45) Date of Patent: Sep. 29, 2015

(54) FBG VIBRATION DETECTION SYSTEM, APPARATUS AND VIBRATION DETECTION METHOD USING THE SYSTEM

(75) Inventor: Hiroshi Tsuda, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 327 days.

(21) Appl. No.: 13/635,587

(22) PCT Filed: Mar. 17, 2011

(86) PCT No.: PCT/JP2011/056373
§ 371 (c)(1),
(2), (4) Date: Sep. 17, 2012

(87) PCT Pub. No.: WO2011/115204
PCT Pub. Date: Sep. 22, 2011

(65) Prior Publication Data
US 2013/0008253 A1   Jan. 10, 2013

(30) Foreign Application Priority Data
Mar. 18, 2010   (JP) ................................ 2010-061986

(51) Int. Cl.
*G01H 9/00* (2006.01)
*G01N 29/14* (2006.01)
(Continued)

(52) U.S. Cl.
CPC ............ *G01B 11/18* (2013.01); *G01D 5/35316* (2013.01); *G01H 9/004* (2013.01); *G01N 29/043* (2013.01); *G01N 29/14* (2013.01)

(58) Field of Classification Search
CPC ..... G01B 11/18; G01H 9/004; G01N 29/043; G01N 29/14; G01D 5/35316
USPC ............................................ 73/587, 597, 655
See application file for complete search history.

(56) References Cited

U.S. PATENT DOCUMENTS 4,709,154 A * 11/1987 Rademaker et al. .......... 250/551
6,356,684 B1 * 3/2002 Patterson et al. ............... 385/37
(Continued)

FOREIGN PATENT DOCUMENTS

JP   2005-009937 A   1/2005
JP   2005-326326 A   11/2005
(Continued)

OTHER PUBLICATIONS

Inamoto et al., "FBG vibration sensor array with temperature compensation using semiconductor optical amplifier tunable laser source", Proceedings of Symposium on Ultrasonic Electronics, vol. 27, Nov. 2006, pp. 261-262.
(Continued)

*Primary Examiner* — J M Saint Surin
(74) *Attorney, Agent, or Firm* — Birch, Stewart, Kolasch & Birch, LLP

(57) ABSTRACT

A vibration detection apparatus for, for example, ultrasound/AE, with Fiber Bragg Grating (FBG), is used for elastic wave detection generated by a material impact and ultrasonic defect detection. Disadvantageously, the apparatus cannot detect ultrasound and has degraded performance at variable temperatures and strains. In response, a highly sensitive, small and light vibration detection apparatus is provided. FBG reflection light is lased by using a fiber laser. The intensity of the lased reflection light from the FBG is converted into an electrical signal. Thus, the ultrasound vibration or the like is detected. A vibration detection system includes an optical amplifier 42, an optical circulator 43, and an optical coupler 45. An FBG 44 and an entry/exit port of the optical circulator are connected by an optical fiber. The optical coupler and the optical amplifier are inserted between an entry port and an exit port of the optical circulator. The entry port and the exit port are connected by an optical fiber.

18 Claims, 26 Drawing Sheets

(51) Int. Cl.
*G01N 29/07* (2006.01)
*G01B 11/16* (2006.01)
*G01D 5/353* (2006.01)
*G01N 29/04* (2006.01)

(56) References Cited

U.S. PATENT DOCUMENTS

| | | | |
|---|---|---|---|
| 6,766,045 B2* | 7/2004 | Slepyan et al. | 382/135 |
| 7,005,630 B2* | 2/2006 | Shin et al. | 250/227.18 |
| 8,040,925 B2* | 10/2011 | Liaw et al. | 372/6 |
| 2004/0149897 A1* | 8/2004 | Tsai et al. | 250/227.14 |
| 2005/0083534 A1* | 4/2005 | Riza et al. | 356/477 |
| 2005/0109922 A1* | 5/2005 | Tsai | 250/227.14 |
| 2009/0161700 A1* | 6/2009 | Mizuuchi et al. | 372/6 |

FOREIGN PATENT DOCUMENTS

| | | |
|---|---|---|
| JP | 2006-132952 A | 5/2006 |
| JP | 2007-240447 A | 9/2007 |
| JP | 2008-046036 A | 2/2008 |
| JP | 2009122994 * | 6/2009 |
| WO | WO2007066747 * | 6/2007 |

OTHER PUBLICATIONS

International Search Report for PCT/JP2011/056373 dated May 10, 2011.

Shin et al., "A comparison of interrogation schemes for impact event monitoring using Fiber Bragg Gratings", Proc. of SPIE, vol. 7493, pp. 749314.1-749314.6, 2009.

Tanaka et al., "Cho-onpa Keisoku Hacho Kirikaegata Hiraki Fiber Laser o Mochiita FBG Shindo Sensor Array", Ultrasonic Technology, pp. 49-53, Nov. 2004.

Tsuda et al., "Strain and damage monitoring of CFRP in impact loading using a fiber Bragg grating sensor system", Composites Science and Technology, vol. 67, pp. 1353-1361, 2007.

Tsuda, "Ultrasound and damage detection in CFRP using fiber Bragg grating sensors", Composites Science and Technology, vol. 66, pp. 676-683, 2006.

* cited by examiner

FBG VIBRATION DETECTION SYSTEM, APPARATUS AND VIBRATION DETECTION METHOD USING THE SYSTEM

TECHNICAL FIELD

The present invention relates to a system for detecting vibration from low frequency vibration to ultrasonic vibration by Fiber Bragg Grating using a fiber laser, and an apparatus and a vibration detection method using the system. The present invention relates to a system useful for, for example, an ultrasonic defect detector, an acoustic emission (AE) sensor, a material (including structure) soundness evaluation apparatus.

BACKGROUND ART

Since ultrasound traversing a material is largely scattered and attenuated at a defect portion, the property of the ultrasound is different depending on whether or not the defect exists. Ultrasonic defect detection is a method for detecting a defect in a material by using the above property. In the ultrasonic defect detection, a piezoelectric device is often conventionally used as an ultrasound sensor. Since a microfracture in a material emits an acoustic emission (AE), detecting the AE allows monitoring a microfracture state in the material. Since the AE is an elastic wave in the ultrasound range, a piezoelectric device is often used as the AE sensor in the same manner as the ultrasound sensor.

Disadvantageously, the piezoelectric device, which is an electric sensor, is affected by electromagnetic interference and cannot be used in a flammable atmosphere. In recent years, Fiber Bragg Grating (hereinafter also referred to as "FBG") has attracted attention as an ultrasound/AE sensor for solving these problems. The FBG is a kind of optical fiber sensors.

An ultrasound or AE detection system that uses the FBG as a sensor is largely divided into two types: the system that uses a laser as a light source; and the system that uses broadband light as a light source. In the case of using the laser, laser lases at a wavelength at which reflectivity of FBG reflection spectrum is largely changed. Such laser is incident on the FBG through an optical circulator. As a result, it is possible to obtain FBG reflection light intensity synchronized with an ultrasound or AE vibration received by the FBG. In the case of using the broadband light, broadband light including an FBG reflection wavelength range is incident on the FBG through an optical circulator. The FBG reflection light is incident on an optical filter with reflection property or transmission property that rapidly changes in the FBG reflection wavelength range. As a result, it is possible to obtain optical filter transmission or reflection light intensity synchronized with an ultrasound or AE vibration. Even when the optical filter is disposed between the broadband light source and the optical circulator, the same effect can be obtained. Non-Patent Document 1 written by the inventor describes an experiment in which each light source is used for ultrasound detection and ultrasonic defect detection in the FBG. Related arts include Patent Documents 1 to 5 by the inventors.

In the structure of the Fiber Bragg Grating (FBG), a core operating as a waveguide of an optical fiber has a refractive index that changes periodically in the fiber axis direction. The FBG reflects narrow-band light around a Bragg wavelength $\lambda_B$ represented by Formula (1).

[Expression 1]

$$\lambda_B = 2n\Lambda \quad (1)$$

Here, n represents a refractive index and $\Lambda$ represents a period interval (grating interval) of the change of the refractive index. When the FBG receives a temperature change or a strain change, the refractive index n and the grating interval $\Lambda$ are changed. Accordingly, the Bragg wavelength $\lambda_B$ is changed (see Formula (1)). The amounts of the Bragg wavelength change caused by the strain change and the temperature change are 1.2 pm/microstrain and 14 pm/° C. respectively in an FBG having the Bragg wavelength in 1.55 μm band generally used in a communication field. An elastic wave such as ultrasound and an AE causes a feeble vibration of about several microstrains at most. If the FBG receives ultrasound wave or an AE, the Bragg wavelength is changed by only about several pm at most. Generally, many of FBGs used to evaluate soundness of structure have a grating length of 1 to 20 mm and the reflection spectrum full width of about 1 to 2 nm at most. If the FBG receives a large temperature or strain change, the Bragg wavelength is largely changed. In a system using a laser light source, the laser wavelength may be therefore outside the reflection wavelength range of the FBG. In a system using a broadband light source, the reflection spectrum of the FBG does not cross over the wavelength range of the optical filter in which the reflection property or the transmission property is rapidly changed. In this case, the ultrasound or the AE received by the FBG cannot be detected.

One possible solution is use of a wavelength variable laser or tunable filter to control the wavelength of the laser or the wavelength at which the optical property of the optical filter changes according to the change of the Bragg wavelength of the FBG. Disadvantageously, the control cannot follow the change of the Bragg wavelength when the Bragg wavelength of the FBG rapidly changes. For this reason, the ultrasound and the AE cannot be detected. The AE in particular is caused by an instantaneous strain change that occurs when the material is broken. Thus, the generation of the AE inevitably accompanies a fast Bragg wavelength change. For this reason, it may be difficult to detect the AE in a measurement system that uses a wavelength variable laser or a tunable filter.

To solve this problem, Patent Document 3 by the inventor ("material soundness evaluation apparatus") discloses a technique for detecting an ultrasound or an AE propagating through a test object without attaching an FBG to the test object. In a conventional detection of ultrasound or AE by the FBG, the FBG is attached to the test object. In contrast, in this technique, a portion other than an FBG in an optical fiber to which the FBG is written is in contact with the test object. The ultrasound or the AE propagating in the test object flows into the optical fiber through a contact point of the optical fiber, propagates in the optical fiber, and ultrasonically vibrates or AE-vibrates the FBG. Since the FBG is not attached to the test object, the Bragg wavelength of the FBG is no longer affected by the strain received by the test object. Nevertheless, the Bragg wavelength of the FBG is inevitably changed by temperature change. As a result, there remains a problem in the detection of the ultrasound and the AE at variable temperatures.

Patent Document 4 by the inventor ("AE/ultrasound detection system, and material monitoring apparatus and nondestructive testing apparatus including the same") discloses an ultrasound/AE detection technique that uses two Fabry-Perot filters and that is independent of the Bragg wavelength of the FBG. In this related art, broadband light is incident on the FBG and reflected light from the FBG is incident on the two Fabry-Perot filters. The two Fabry-Perot filters have a free spectral range (FSR: interval of transmittance peak wavelengths of Fabry-Perot filter with periodic transmission property) that is substantially the same as the reflection spectrum full width of the FBG. In addition, the two Fabry-Perot filters have transmittance peak wavelengths different from each other by FSR/4. In this technique, the transmission light intensity of at least one Fabry-Perot filter varies in synchronization with the ultrasound or AE vibration received by the FBG regardless of the Bragg wavelength of the FBG. For this reason, it is possible to detect the ultrasound or the AE independently of the change of the Bragg wavelength.

There are two requirements in the ultrasound/AE detection system described in Patent Document 4: First, two Fabry-Perot filters have an FSR that is substantially the same as the reflection spectrum full width of the FBG; Second, the transmittance peak wavelengths of the two Fabry-Perot filters are shifted from each other by FSR/4. Yet, the first requirement presents difficult to accurately control the reflection spectrum full width of the FBG and the FSR of the Fabry-Perot filters in a manufacturing process of these. Thus, expensive system constituent elements may be required. Further, to shift the transmittance peak wavelengths of the two Fabry-Perot filters from each other by FSR/4 (second requirement), it is necessary to attach a temperature adjustment unit for controlling the transmittance peak wavelength to the Fabry-Perot filters or prepare a large number of Fabry-Perot filters and select two Fabry-Perot filters whose transmittance peak wavelengths are shifted from each other by FSR/4 from the prepared Fabry-Perot filters. As described above, in the technique of Patent Document 4, there are problems that the system constituent elements are expensive and the number of the system constituent elements increases.

RELATED DOCUMENT

Patent Document

Patent Document 1: Japanese Laid-open patent publication No. 2005-326326
Patent Document 2: Japanese Laid-open patent publication No. 2005-009937
Patent Document 3: Japanese Laid-open patent publication No. 2007-240447
Patent Document 4: Japanese Laid-open patent publication No. 2008-046036
Patent Document 5: Japanese Laid-open patent publication No. 2006-132952

Non-Patent Document

Non-Patent Document 1: Hiroshi Tsuda, "Ultrasound and Damage Detection in CFRP using Fiber Bragg Grating Sensors", Composites Science and Technology, Vol. 66, p. 676-683 (2006)
Non-Patent Document 2: Hiroshi Tsuda and Jung-Ryul Lee, "Strain and Damage Monitoring of CFRP in Impact Loading Using a Fiber Bragg Grating Sensor System", Composites Science and Technology, Vol. 67, p. 1353-1361 (2007)

SUMMARY OF THE INVENTION

Problems to be Solved by the Invention

The inventor has already filed a patent application directed to improvement of a conventional ultrasound/AE detection system that uses broadband light as a light source (Japanese Patent Application No. 2010-011526 "Vibration detection system, and apparatus and vibration detection method using the system", hereinafter referred to as "related patent application"). The related patent application describes an ultrasound/AE detection technique at variable strains and temperatures. The technique does not require the optical filter in a conventional ultrasound/AE detection system that uses broadband light as a light source. In this technique, the broadband light is incident on the FBG. The FBG reflection light intensity is converted into an electrical signal. The ultrasound/AE received by the FBG is detected by an averaging process and an appropriate frequency filtering process of the electrical signal. The strategic attachment of the FBG to the test object allows the FBG to have resonant property, thereby improving the ultrasound/AE detection sensitivity. Since the ultrasound/AE detection system based on the technique has a small number of constituent elements and has no expensive element, the ultrasound/AE detection system can be assembled as a small and light system at a low cost.

A sixth embodiment of the related patent application demonstrates, with the intention of AE detection, an experiment result in which ultrasound propagating in a material is detected without the averaging process of the response signal. It is described that the FBG sensor with resonant property to bandpass filter a sensor signal for allowing passage near the resonant frequency of the sensor enables detecting the ultrasound without the averaging process. To detect every ultrasound/AE disadvantageously requires bandpass filtering of the sensor signal for each of plural resonant frequencies of the sensor, thereby resulting in complicated signal processing. The S/N ratio of a detected response signal is so low that a trigger setting for recording a signal may be not easy when an ultrasound/AE response waveform is recorded. Since an FBG sensor with a non-resonant structure in which the FBG is in contact with the test object cannot detect the ultrasound/AE without the averaging process, further improvement of the detection sensitivity of the ultrasound/AE is required.

The present invention solves the above problems, and an object of the present invention is to provide a highly reliable detection system for detecting an ultrasound or an AE at variable strains and temperatures. In addition, an object of the present invention is to improve detectability of an ultrasound or an AE. In addition, an object of the present invention is to realize a system that has a small number of constituent elements and has no expensive element and that can be assembled as a small and light system at a low cost.

Solution for Solving Problems

To solve the above problems, the present invention configures a fiber laser using an FBG (a sensor) as a reflection mirror to form high intensity and narrow band FBG reflection light. In other words, a laser having the Bragg wavelength of FBG at a lasing wavelength is obtained. In the present specification, hereinafter, forming high intensity and narrow band FBG reflection light by using a fiber laser is referred to as lasing FBG reflection light. The lased reflection light from the FBG is incident on an opto-electrical converter to convert the reflection light intensity into an electrical signal. Thus, a response signal corresponding to the ultrasound/AE received by the FBG is obtained.

In the present invention, an FBG sensor is allowed to have a resonant structure by attaching a part of an FBG of an optical fiber to which the FBG sensor is written or a portion of the optical fiber other than the FBG to a test object. Control of the sensor response frequency property and detectability of ultrasound/AE can be further improved by using the FBG sensor with a resonant structure.

The significance of the present invention will be described.

FIG. 25 shows wavelength dependence of light output of the broadband light source used in the experiment described in the related patent application by the inventor. At this time, an FBG having the Bragg wavelength of 1,550 nm is used in the experiment. The light output near the wavelength of 1,550 nm decreases somewhat with the increase in the wavelength. Thus, the technique described in the related patent application uses the slight wavelength-dependence of the light output in the broadband light source. Then, a slight change of the FBG reflection light intensity following the change of the Bragg wavelength caused by an ultrasound is converted into an electrical signal and detected by the frequency filtering process and the averaging process. Since ultrasound can be detected by using the slight wavelength-dependence of a light output of the light source, increasing the intensity of the FBG reflection light may be an effective means to improve the sensitivity of the ultrasound detection. For example, as shown in FIG. 26, the Bragg wavelength is to oscillate between a wavelength A and a wavelength B and the light output varies between 1 and 0.5 by ultrasound oscillation. If the light source can obtain FBG reflection light intensity of 10 at the wavelength A, the reflection light intensity varies from 10 to 5 occurs by the ultrasonic oscillation. As a result, the change of the light intensity caused by the ultrasound oscillation is 5. Next, if the light source can obtain FBG reflection light intensity of 100 at the wavelength A, the reflection light intensity varies from 100 to 50 occurs by the ultrasound oscillation. As a result, the light intensity caused by the ultrasound oscillation is 50. Thus, the use of a light source that can obtain a high intensity FBG reflection light may enhance the sensitivity of the ultrasound detection, because the light intensity is largely changed by the ultrasound oscillation. A corollary to this is the idea that a fiber laser that can obtain laser light at the Bragg wavelength of the FBG is used as a light source.

To achieve the above objects, the present invention has the features described below.

The present invention is a vibration detection system for detecting vibration, the system comprising: a fiber laser; a Fiber Bragg Grating (hereinafter referred to as FBG) operating as a reflection mirror of the fiber laser; and an opto-electrical conversion unit converting intensity of reflection light from the FBG into an electrical signal, the reflection light being lased by the fiber laser. The present invention is to detect vibration with a frequency lower than or equal to 20 kHz including vibration of sub-Hz, ultrasound, or an acoustic emission. The vibration detection system according to the present invention includes: an optical amplifier; an optical circulator; and an optical coupler. The fiber laser is has a lasing wavelength at the Bragg wavelength of the FBG, the Bragg wavelength being determined by the optical amplifier capable of optical amplification in a wavelength range that comprises a reflection wavelength of the FBG by using the FBG for a sensor operating as a reflection mirror. Specifically, the FBG and an entry/exit port of the optical circulator are connected by an optical fiber; the optical coupler and the optical amplifier are inserted between an entry port and an exit port of the optical circulator; and the entry port and the exit port are connected by an optical fiber. Reflection light from the FBG traverses a ring-shaped optical fiber through the optical circulator, wherein the optical coupler and the optical amplifier are inserted into the ring-shaped optical fiber; the reflection light is amplified by the optical amplifier, incident on the FBG through the optical circulator, and reflected again by the FBG; and amplification of the FBG reflection light is repeated in an optical fiber ring-shaped portion in which the optical amplifier is inserted, thereby generating a laser having a lasing wavelength at the Bragg wavelength of the FBG.

The vibration detection system of the present invention is to allow an FBG sensor to have resonant property. An FBG sensor is allowed to have resonant property by contact of a test object with a part of the FBG of an optical fiber to which the FBG is written or a portion of the optical fiber other than the FBG. Thus, it is possible to control the response frequency property of the sensor. Vibration is transmitted to the optical fiber through a portion in contact with the test object. The resonant frequency can be controlled by adjusting the length of the optical fiber resonant portion. In addition, the frequency property of the ultrasound/AE detection sensitivity can be controlled.

The vibration detection system according to the present invention may include an optical filter. In the vibration detection system according to the present invention, the fiber laser may include an amplifying medium between FBGs having the same Bragg wavelength.

The vibration detection system according to the present invention includes a signal processing unit, the signal processing unit frequency filtering the electrical signal converted by the opto-electrical conversion unit. For example, the frequency filtering is bandpass filtering near a resonant frequency band based on resonant property.

The vibration detection system of the present invention can have a movable configuration. In a non-resonant structure, a movable FBG sensor is formed by touching an FBG to a medium where ultrasound propagation speed is slower than that in the test object or a thin medium having a thickness of 1 mm or less. The movable FBG sensor may be touched to the test object. In a resonant structure, a movable FBG sensor with resonant property is formed by touching a part of an FBG of an optical fiber to which the FBG is written or a portion of the optical fiber other than the FBG to a medium where ultrasound propagation speed is slower than that in the test object or a thin medium having a thickness of 1 mm or less. The movable FBG sensor may be touched to the test object.

The vibration detection system of the present invention includes a plurality of the FBGs, wherein a multi-point measurement is performed. An ultrasound propagation state is measured using the vibration detection system of the present invention. A material soundness evaluation apparatus that evaluates soundness of a test object, an ultrasonic defect detection apparatus, or an apparatus that detects an acoustic emission generated when a material is broken is provided. In addition, the vibration detection system of the present invention provides an apparatus that detects a low frequency vibration of sub-Hz and an impact load. A low frequency vibration and an impact load are detected using the vibration detection system of the present invention. An apparatus for diagnosis of machine failure and anti-crime/anti-disaster is provided. Further, it is possible to determine an impact position by performing a multi-point measurement.

A vibration detection method according to the present invention an FBG operating as a reflection mirror of a fiber laser, wherein a vibration is detected by converting intensity of light reflected from the FBG into an electrical signal, the reflected light being lased by the fiber laser.

Effect of the Invention

The present invention enables detecting ultrasound and an AE by using an FBG even at variable strains and temperatures. In addition, the present invention enables, with a small number of the system constituent elements, realizing a small, light, and low cost system and improving reliability. In addition, the present invention enables detecting an ultrasound/AE response in a highly sensitive manner from the change of the light intensity of the FBG reflection light that is lased by the fiber laser. In addition, an FBG sensor with a resonant structure enables improving detectability of ultrasound or an AE and controlling the frequency property of the response waveform.

The present invention enables detecting vibration from low frequency vibration of sub-Hz order to ultrasound range higher than 20 kHz. Since the ultrasound can be detected without the averaging process of the response signal, the acoustic emission (AE) that is emitted when a material fracture occurs can be accurately detected. When a response signal is obtained using a periodic ultrasonic vibration, the FBG sensor with a resonant structure shows a response having a high component intensity at the resonant frequency near the frequency of the received ultrasound. For this reason, the detectability of ultrasound or an AE can be further improved by an appropriate frequency filtering process.

In addition, the present invention can be an apparatus useful for test a test object by the movable FBG sensor.

In addition, the present invention enables arranging a plurality of FBG sensors in one optical fiber line by using a wavelength separation technique, thereby constructing a very simple vibration detection sensor network.

BRIEF DESCRIPTION OF THE DRAWINGS

In FIG. 5, (a) is a diagram showing the response waveform when the frequency of the sine wave is 100 kHz, (b) is a diagram showing the response waveform when the frequency of the sine wave is 200 kHz, (c) is a diagram showing the response waveform when the frequency of the sine wave is 300 kHz, and (d) is a diagram showing the response waveform when the frequency of the sine wave is 400 kHz.

In FIG. 6, (a), (b), (c), and (d) correspond to (a), (b), (c), and (d) of FIG. 5, respectively.

In FIG. 7, (a) is a diagram showing the response waveform when the frequency of the sine wave is 100 kHz, (b) is a diagram showing the response waveform when the frequency of the sine wave is 200 kHz, (c) is a diagram showing the response waveform when the frequency of the sine wave is 300 kHz, and (d) is a diagram showing the response waveform when the frequency of the sine wave is 400 kHz.

In FIG. 8, (a), (b), (c), and (d) correspond to (a), (b), (c), and (d) of FIG. 7, respectively.

In FIG. 11, (a) is a response waveform on which a low pass filtering process of 500 kHz is performed using the system proposed in the related patent application shown in FIG. 3, (b) is a response waveform on which a bandpass filtering process of 170 kHz is performed using the system proposed in the related patent application shown in FIG. 3, and (c) is a response waveform on which a bandpass filtering process of 30 kHz to 500 kHz is performed using the system shown in FIG. 9.

In FIG. 20, (a) is a response signal of an FBG sensor with a non-resonant structure and (b) is a response signal of an FBG sensor with a resonant structure.

In FIG. 21, (a) is a strain curve measured by a strain gauge and (b) is a diagram showing output of an FBG sensor.

DESCRIPTION OF EMBODIMENTS

Figure 1:
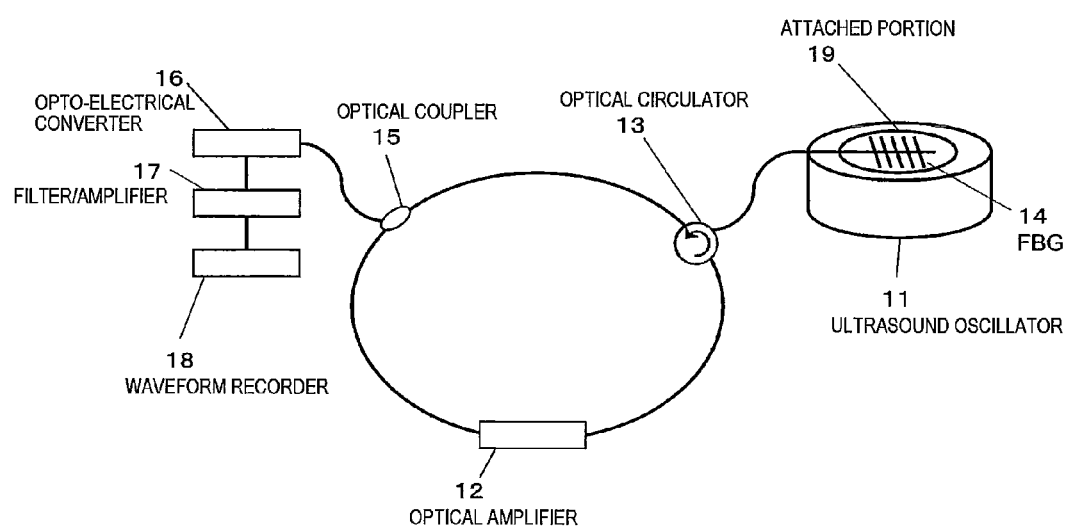
FIG. 1 is a diagram showing a system used for an ultrasound measurement experiment corresponding to a first embodiment of the present invention.

The present invention relates to a system for detecting vibration from low frequency vibration of sub-Hz (lower than 1 Hz) order to ultrasound range higher than 20 kHz. The present invention is a system for detecting vibration up to 20 kHz and an ultrasound with a frequency of 20 kHz or higher. The present invention can be applied to ultrasound detection, AE detection, an ultrasonic defect detector using these detection, an acoustic emission (AE) sensor, and a material (structure) soundness evaluation apparatus. Hereinafter, embodiments of the present invention will be described.

(First Embodiment)

A first embodiment is a basic form of ultrasound response detection using an FBG sensor. An ultrasound detection system of the present embodiment is best characterized by lasing reflection light from the FBG by a fiber laser and detecting ultrasound received by the FBG. The ultrasound detection system of the present embodiment includes an optical amplifier, an optical circulator, an FBG, an optical coupler, an opto-electrical converter, and a waveform recorder. In the ultrasound detection system of the present embodiment, the FBG and an entry/exit port of the optical circulator are connected by an optical fiber. The optical coupler and the optical amplifier are inserted between an entry port and an exit port of the optical circulator. The entry port and the exit port are connected by an optical fiber. The reflection light from the FBG traverses a ring-shaped optical fiber through the optical circulator. The optical coupler and the optical amplifier are inserted into the ring-shaped optical fiber. The reflection light is amplified by the optical amplifier, and is incident on the FBG through the optical circulator. Then, the reflection light is reflected again by the FBG. Such amplification of the FBG reflection light is repeated in the optical fiber ring-shaped portion in which the optical amplifier is inserted. Thus, a laser having the Bragg wavelength of the FBG at a lasing wavelength is generated. In other words, the FBG operating as a reflection mirror constitutes a fiber laser. Apart of the lased FBG reflection light is extracted from the optical coupler, incident on the opto-electrical converter, thus being converted into an electrical signal. The electrical signal is filtered and amplified as needed, and thereafter recorded in the waveform recorder. In the present embodiment, the electrical signal from the opto-electrical converter is averaged. Thus, the ultrasound received by the FBG is detected and displayed on a display unit of the waveform recorder or recorded in a recording device of the waveform recorder. In the averaging process, as shown in the experiment described below, multiple signal averaging is performed on a response signal waveform to the ultrasound excited by input of an excitation signal to an ultrasound oscillator. For example, the signal averaging may be performed by an averaging processor that uses an excitation signal from a spike excitation ultrasound oscillator, as a trigger. The waveform recorder may be capable of averaging process.

Figure 2:
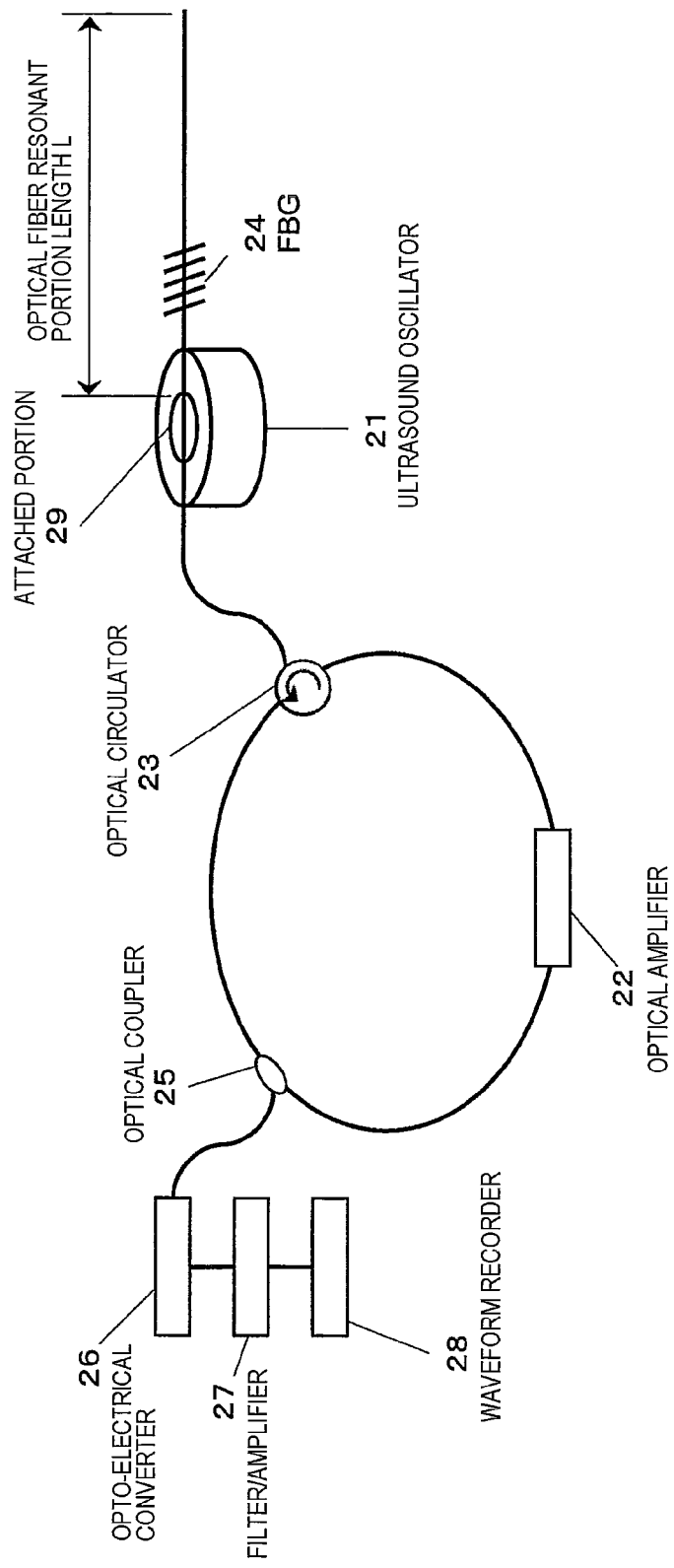
FIG. 2 is a diagram showing a system used for an ultrasound measurement experiment corresponding to a second embodiment of the present invention.

FIGS. 1 and 2 are schematic diagrams of systems used in an ultrasound measurement experiments for explaining the vibration detection system of the present invention. FIGS. 1 and 2 are diagrams for understanding of a first embodiment and a second embodiment. The ultrasound measurement experiment system shown in FIG. 1 includes an optical amplifier 12, an optical circulator 13, an FBG 14, an optical coupler 15, an ultrasound oscillator 11, an opto-electrical converter 16, a filter/amplifier 17, and a waveform recorder 18. An optical fiber is attached to the ultrasound oscillator 11 at an attached portion 19. The ultrasound measurement experiment system shown in FIG. 2 includes an optical amplifier 22, an optical circulator 23, an FBG 24, an optical coupler 25, an ultrasound oscillator 21, an opto-electrical converter 26, a filter/amplifier 27, and a waveform recorder 28. An optical fiber with the FBG is attached to the ultrasound oscillator 21 at an attached portion 29.

The ultrasound measurement experiment system will be described below with reference to FIG. 1. In the ultrasound measurement experiment system shown in FIG. 1, the FBG 14 and an entry/exit port of the optical circulator 13 are connected by an optical fiber. The optical coupler 15 and the optical amplifier 12 are inserted between an entry port and an exit port of the optical circulator 13. The entry port and the exit port are connected by an optical fiber. The reflection light from the FBG 14 traverses the ring-shaped optical fiber through the optical circulator 13. The optical coupler 15 and the optical amplifier 12 are inserted into the ring-shaped optical fiber. The reflection light is amplified by the optical amplifier 12, and is incident on the FBG 14 through the optical circulator 13. Then, the reflection light is reflected again by the FBG 14. Such amplification of the FBG reflection light is repeated in the optical fiber ring-shaped portion in which the optical amplifier 12 is inserted. Thus, a laser having the Bragg wavelength of the FBG at a lasing wavelength is generated. In other words, the FBG 14 operating as a reflection mirror constitutes a fiber laser. A part of the lased FBG reflection light is extracted from the optical coupler 15, incident on the opto-electrical converter 16, and converted into an electrical signal. The electrical signal is filtered and amplified as needed, and thereafter recorded in the waveform recorder 18. The systems shown in FIGS. 1 and 2 are characterized in that a fiber laser replaces the light source of the detection system using the broadband light source described in the related patent application shown in FIG. 3. An ultrasound measurement experiment system described in the related patent application shown in FIG. 3 includes a broadband light source 2, an optical circulator 3, an FBG 4, an ultrasound oscillator 1, an opto-electrical converter 5, an amplifier 6, a filter 7, and a waveform recorder 8. An optical fiber with the FBG is attached to the ultrasound oscillator 21 at an attached portion 9.

Figure 3:
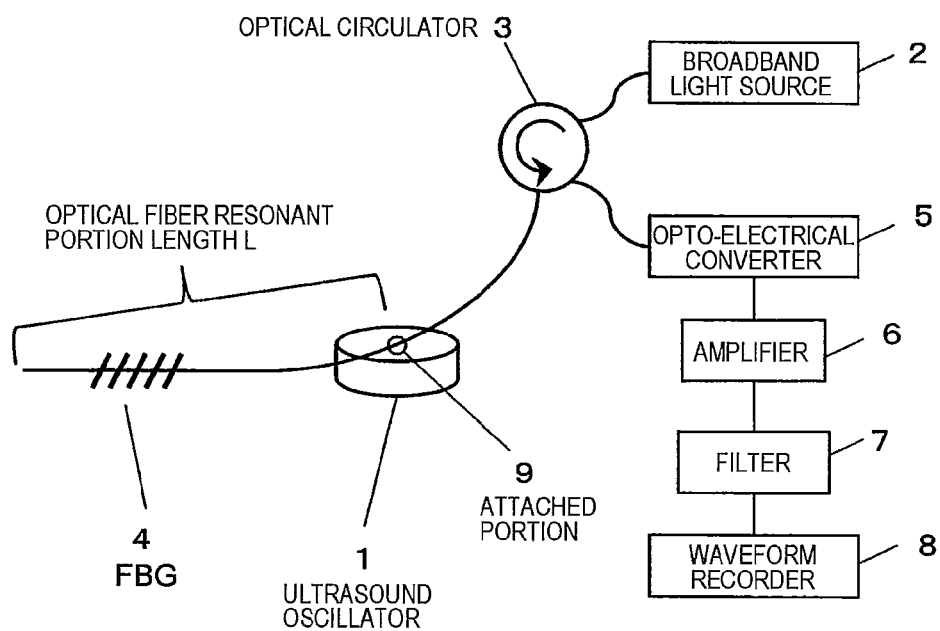
FIG. 3 is a diagram showing a vibration detection system disclosed in a related patent application.
Figure 4:
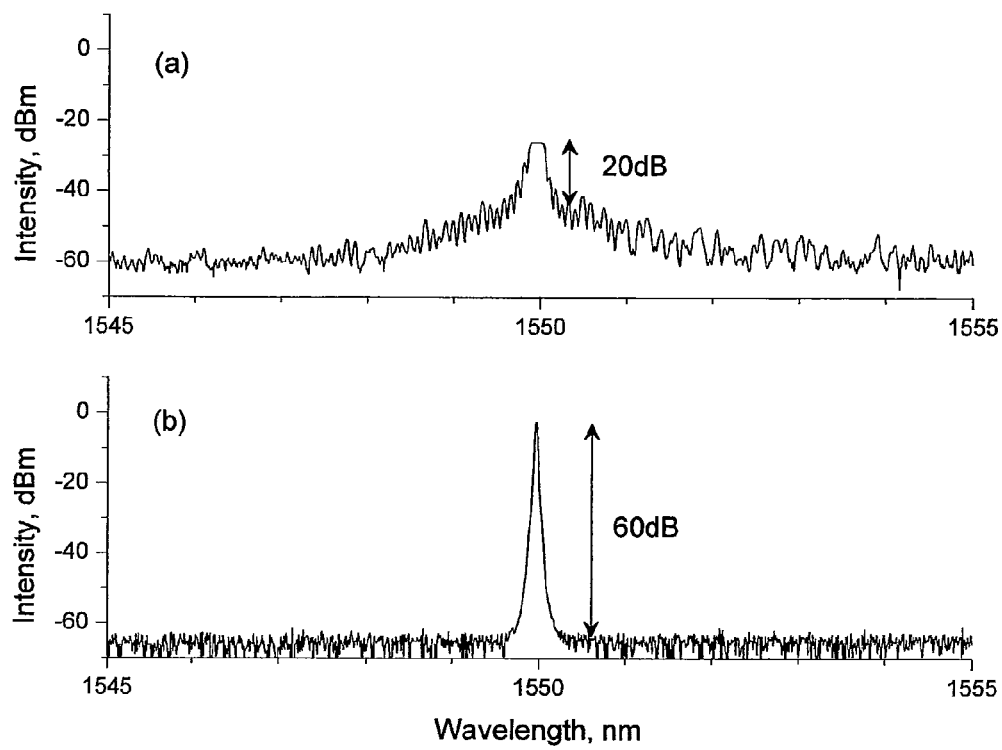
FIG. 4(a) is a diagram showing an FBG reflection spectrum is incident on an opto-electrical converter when broadband light is used as a light source (the system shown in FIG. 3).
FIG. 4(b) is a diagram showing an FBG reflection spectrum is incident on an opto-electrical converter when a fiber laser is used (the systems shown in FIGS. 1 and 2) as a light source.

FIG. 4(a) shows an FBG reflection spectrum incident on the opto-electrical converter when broadband light shown in FIG. 3 is used as a light source. FIG. 4(b) shows an FBG reflection spectrum incident on the opto-electrical converter when the fiber laser shown in FIGS. 1 and 2 is used as a light source. The FBG reflection light is lased by the fiber laser. As a result, the FBG reflection light is intensified and becomes a narrower band spectrum of which the center is the Bragg wavelength. As shown in FIG. 4, when a commercially available broadband light source is used (FIG. 4(a)), the S/N ratio of the FBG reflection light power is about 20 dB. On the other hand, when the fiber laser is used (FIG. 4(b)), reflection light having an S/N ratio of 60 dB or more can be obtained.

To propagate ultrasound in an optical fiber to which an FBG is written, a part of the optical fiber is attached to the ultrasound oscillator as shown in FIGS. 1 and 2. The ultrasound oscillator ultrasonically vibrates by input of an excitation signal. The ultrasound flows in the optical fiber through the attached portion. In FIG. 1, the FBG is attached to the ultrasound oscillator. In FIG. 2, a part of an optical fiber with an FBG is attached to the ultrasound oscillator. The optical fiber with an FBG (also referred to as an FBG sensor) detects ultrasound propagating bi-directionally between the optical fiber attached point and the optical fiber free end. Thus, the response of the optical fiber indicates a resonant property. In the present invention, the length from the optical fiber attached point to the free end is defined as "optical fiber resonant portion length". FIG. 2 illustrates an optical fiber resonant portion length L.

The grating length of the FBG used in the present embodiment is 10 mm. Also in the other embodiments described in this specification, an FBG having a length of 10 mm is used. The used optical amplifier is a C band (1530 to 1565 nm) erbium-doped optical fiber amplifier, capable of amplifying light in the C band.

When a periodic sine wave is used as the excitation signal input into the ultrasound oscillator, the frequency of the oscillated ultrasound corresponds to the frequency of the excitation signal sine wave. In other words, the frequency of the oscillated ultrasound can be controlled. Here, the effect of the ultrasound frequency on the response signal of the FBG sensor is evaluated. For this reason, the response signals to ultrasound excited by sine waves of three cycles from 100 kHz to 400 kHz are recorded.

Figure 5:
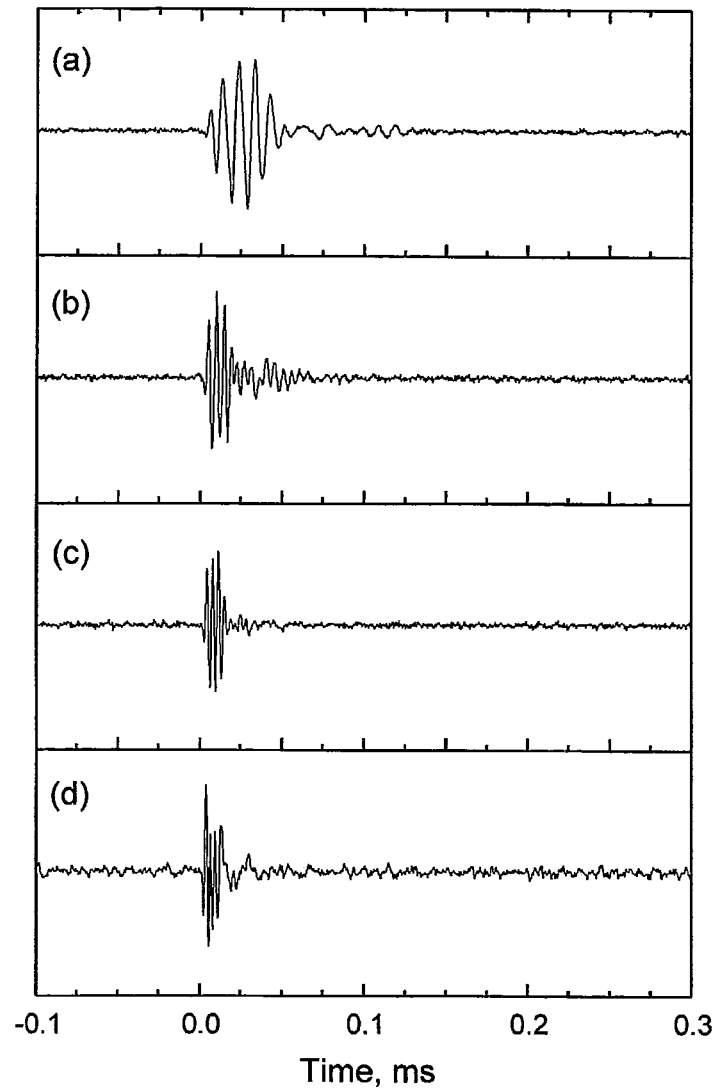
FIG. 5 is response waveforms of an FBG sensor with a non-resonant structure to three cycle sine wave excitation ultrasound where the frequency is changed in the system shown in FIG. 1.
Figure 6:
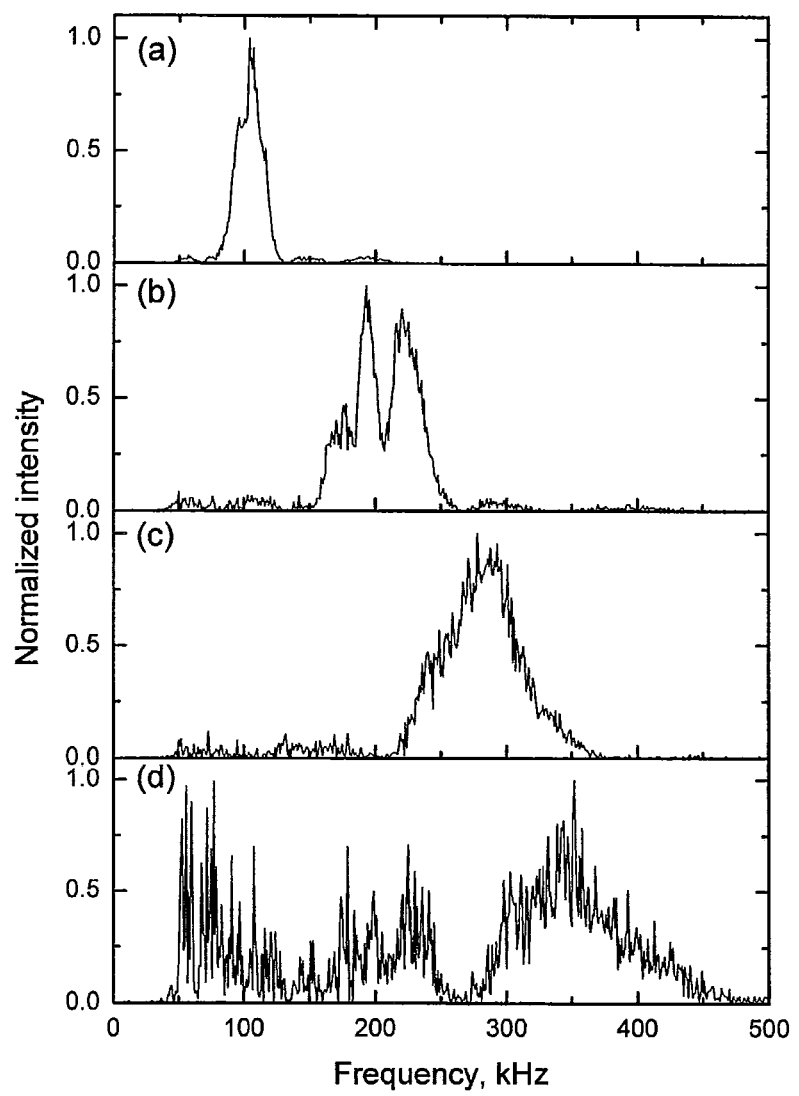
FIG. 6 is diagrams showing the frequency property of the response waveforms shown in FIG. 5.

An FBG sensor with the optical fiber resonant portion length of 0 mm, that is, an FBG sensor with a non-resonant structure attached to the ultrasound oscillator in the full length of the FBG is used to record the response signals to the ultrasound generated by excitation of the ultrasound oscillator of which the central frequency is 250 kHz by sine waves of three cycles from 100 kHz to 400 kHz. In FIG. 5, (a) to (d) show response waveforms recorded by bandpass filtering of 50 kHz to 1 MHz and 512 times averaging by using the system shown in FIG. 1, with the frequency of the ultrasound excitation sine wave signal being 100 kHz, 200 kHz, 300 kHz, and 400 kHz. In FIG. 6, (a) to (d) show the frequency property of each response waveform. A response duration time of the ultrasound response of the FBG sensor with a non-resonant structure is short. The response signal has broadband frequency property and the center of the response signal is at the ultrasound frequency.

(Second Embodiment)

The second embodiment is different from the first embodiment in a point that the FBG sensor has a resonant structure. The other configuration is the same as that of the first embodiment. The ultrasound detection system of the second embodiment includes an optical amplifier, an optical circulator, an FBG, an optical coupler, an opto-electrical converter, and a waveform recorder in the same manner as in the first embodiment. In a vibration detection system of the present embodiment, the FBG sensor is allowed to have resonant property by touching a part of an FBG of an optical fiber to which the FBG is written or a portion of the optical fiber other than the FBG to the test object. The ultrasound vibration is transmitted to the optical fiber through a portion in contact with the test object. A part of the lased FBG reflection light is extracted from the optical coupler, incident on the opto-electrical converter, and converted into an electrical signal.

To describe the second embodiment, an ultrasound measurement experiment that is the same as that shown in FIG. 1 except for the structure of the FBG sensor will be described with reference to FIG. 2.

Figure 7:
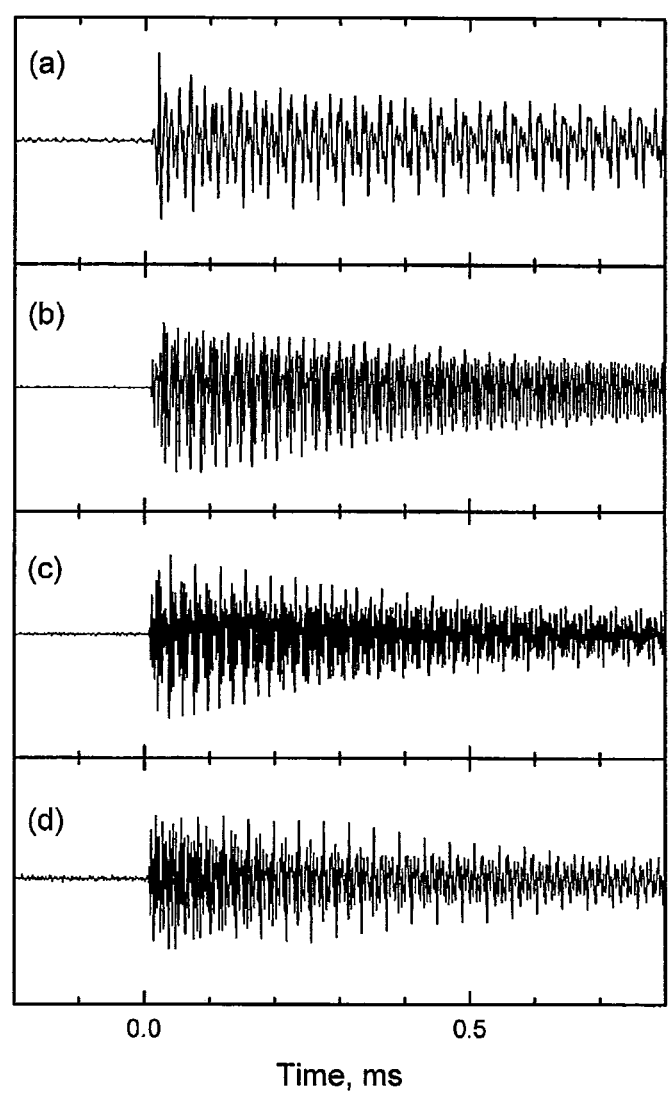
FIG. 7 is response waveforms of an FBG sensor with a resonant structure, in which the length of an optical fiber resonant portion is 50 mm, to three cycle sine wave excitation ultrasound where the frequency is changed in the system shown in FIG. 2.
Figure 8:
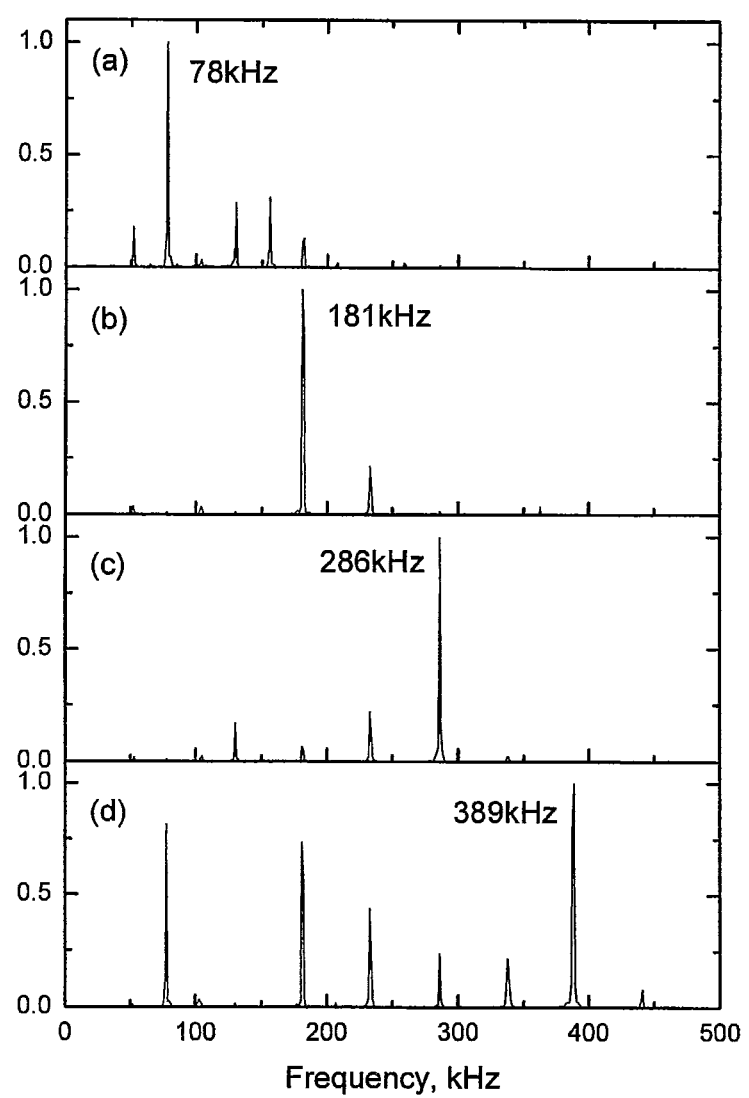
FIG. 8 is diagrams showing the frequency property of the response waveforms shown in FIG. 7.

An FBG sensor with a resonant structure having the optical fiber resonant portion length of 50 mm is used to record response signals to ultrasound generated by excitation of the ultrasound oscillator of which the central frequency is 250 kHz by sine waves of three cycles from 100 kHz to 400 kHz. In FIG. 7, (a) to (d) show response waveforms recorded by bandpass filtering process of 50 kHz to 1 MHz and 512 times averaging processes by using the system shown in FIG. 2, with the frequency of the ultrasound excitation sine wave signal being 100 kHz, 200 kHz, 300 kHz, and 400 kHz. In FIG. 8, (a) to (d) show the frequency characteristics of each response waveform. An FBG sensor with a resonant structure detects ultrasound propagating bi-directionally in the optical fiber resonant portion. For this reason, such an FBG is known to indicate a response of which the response intensity attenuates gradually. This characteristic can be confirmed also from FIG. 7.

When the FBG sensor is attached as shown in FIG. 2, the FBG sensor 24 exhibits the same resonant property as that of a cantilever beam of which beam length is the optical fiber resonant portion length. The resonant frequency $f_{r,n}$ is provided by Formula (2).

[Expression 2]

$$f_{r,n} = \frac{(2n+1)v}{4L}, n = 0, 1, 2, \ldots \quad (2)$$

Here, v and L are an ultrasound propagation speed in the optical fiber and the optical fiber resonant portion length respectively.

The used optical fiber is the same type as that used in the related patent application and the ultrasound propagation speed of the optical fiber is evaluated to be 5,060 m/s. The resonant frequency of which the degree n is 1 to 7 and which is calculated by substituting the ultrasound propagation speed 5,060 m/s into Formula (2) is 75.9, 127, 177, 228, 278, 329, and 380 kHz.

The response signal with the excitation signal frequency being 100, 200, 300, and 400 kHz has a high intensity of the frequency component near the resonant frequency close to the excitation signal frequency (numbers in FIG. 8 indicate frequencies at which the maximum component intensity appears). This is the same result as that of the fourth embodiment of the related patent application (an embodiment that uses broadband light as a light source and that uses an effect of the ultrasound frequency on the ultrasound response of the FBG sensor with a resonant property).

The above describes the response result of the FBG sensor with a non-resonant structure (first embodiment) and a resonant structure (second embodiment) to the ultrasound propagating in the optical fiber, with an optical fiber to which an FBG is written being attached to the surface of the ultrasound oscillator. The same result as that of the related patent application can be obtained.

In the present invention, a fiber laser using an FBG as a reflection mirror for a sensor is used as a light source. Ultrasound vibration received by the sensor is detected as an intensity change of the lased FBG reflection light. The fiber laser lases at the Bragg wavelength at all times independently from the strain received by the FBG and the temperature change. As a result, it is possible to detect ultrasound regardless of the strain received by the FBG and the temperature.

In the embodiments of the present invention, an erbium-doped optical fiber amplifier, that is, a rare-earth-doped optical fiber amplifier, is used as an optical amplifier. It is obvious that the same effect can be obtained by using a fiber Raman amplifier or a semiconductor light amplifier is used or a combination of these.

In the embodiments of the present invention, examples of the FBG sensor with a resonant structure include only a case in which the FBG is located between the portion at which the optical fiber is attached to the test object and the free end. It is obvious that the FBG functions as the FBG sensor with a resonant structure even when the FBG is located between the portion at which the optical fiber is attached to the test object and the optical circulator.

(Third Embodiment)

Figure 9:
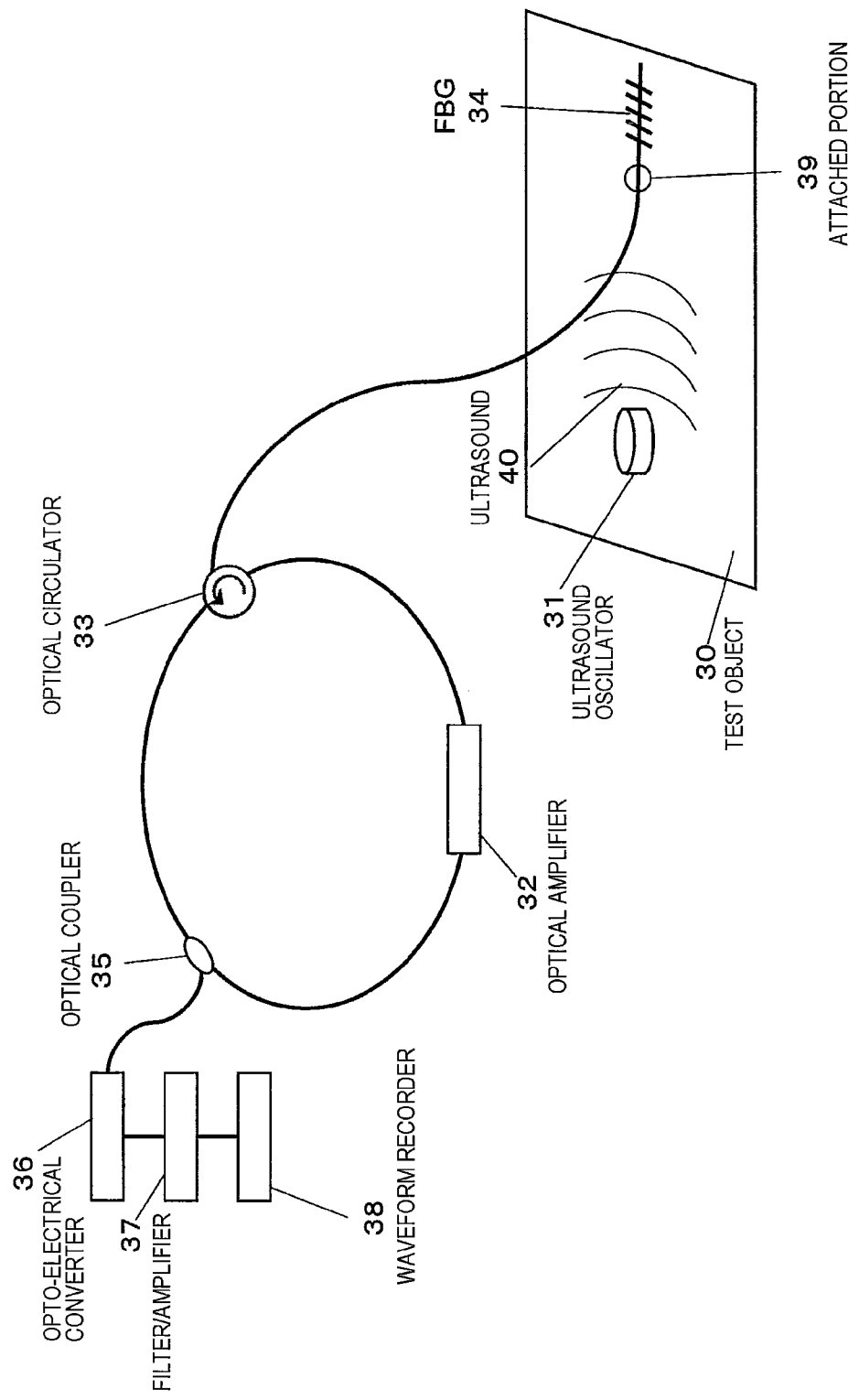
FIG. 9 is a diagram showing a system of a third embodiment.

In a third embodiment, the ultrasound detection system described in the second embodiment is applied to detection of an ultrasound propagating in a material. The third embodiment demonstrates an example of the detection sensitivity of the ultrasound detection system. FIG. 9 shows a system of the third embodiment. The system shown in FIG. 9 includes an optical amplifier 32, an optical circulator 33, an FBG 34, an optical coupler 35, an ultrasound oscillator 31, an opto-electrical converter 36, a filter/amplifier 37, and a waveform recorder 38. An optical fiber including the FBG is attached to a test object 30 at an attached portion 39. The ultrasound oscillator 31 is fixed to the test object 30.

The sensitivity of the ultrasound detection based on the technique disclosed in the related patent application and the sensitivity of the ultrasound detection based on the technique proposed by the present embodiment are compared. The sixth embodiment of the related patent application demonstrates that ultrasound propagating in a material can be detected by an FBG sensor with a resonant structure, without the averaging process. The experiment setup shown in FIG. 9 is prepared to obtain the ultrasound response in accordance with the present embodiment under the same condition as the sixth embodiment of the related patent application regarding the ultrasound oscillator, ultrasound excitation signal, distance between the ultrasound oscillator and the optical fiber attached position, and material that allows passage of the ultrasound. An aluminum plate with a thickness of 1 mm is used as the test object 30. The distance between the ultrasound oscillator and the optical fiber attached position is set to 150 mm. The ultrasound oscillator 31 with the central frequency 250 kHz is excited by a spike wave. Thus, the ultrasound 40 traverses the test object 30. The used FBG sensor 34 has a resonant structure having the grating length of 10 mm and the optical fiber resonant portion length of 38.5 mm. The sixth embodiment of the related patent application uses an FBG sensor having the grating length of 20 mm and the optical fiber resonant portion length of 22 mm. In practice, however, the ultrasound detection sensitivity may be largely immune to the grating length and the optical fiber resonant portion length.

Figure 10:
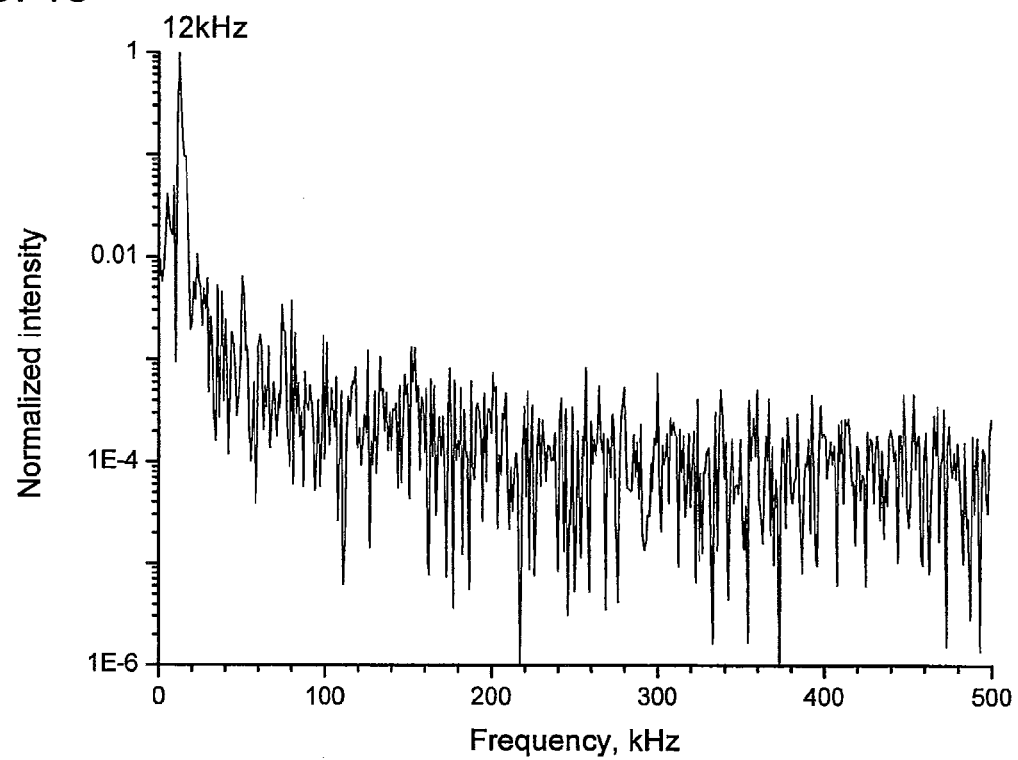
FIG. 10 is a diagram showing the frequency property of a background noise in the system of the third embodiment.

FIG. 10 shows an FBG sensor output without the presence of the propagating ultrasound in the experiment setup shown in FIG. 9, that is, the frequency property of a background noise. The noise has the maximum component intensity at 12 kHz. The noise level is smaller than or equal to 1% of the maximum component intensity in a frequency range of 30 kHz or higher. In the experiment setup shown in FIG. 9, a bandpass of the filter is set to 30 kHz to 500 kHz. In addition, the spike wave excitation ultrasound propagating in the test object is recorded without the averaging process.

Figure 11:
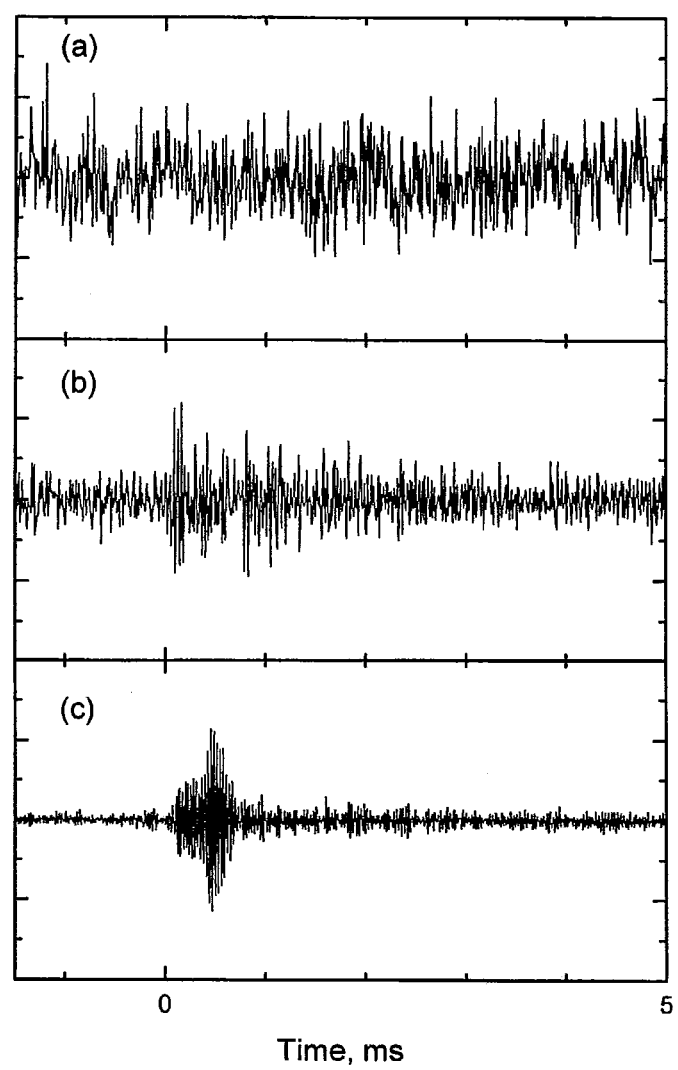
FIG. 11 is response waveforms of an FBG sensor with a resonant structure to ultrasound propagating in a material.

In FIG. 11, (a) and (b) show the response signal of the sixth embodiment of the related patent application (an example in which the vibration detection system in FIG. 3 is applied to the AE detection), and (c) shows the response signal obtained from the system proposed by the present embodiment. In FIG. 11, (a) is the response waveform when the filter is set to a low pass filter with the cut-off frequency of 500 kHz in the example in which the vibration detection system (see FIG. 3) of the related patent application is applied to the AE detection. The system proposed in the related patent application cannot identify the ultrasound response without the averaging the response signal and with the low pass filtering process. The related patent application (paragraphs 75 and 76) demonstrates that the frequency component intensity of the response waveform in FIG. 11(a) shows a high component intensity at a primary resonant frequency of 173 kHz (obtained by substituting n=1, v=5,060 m/s, and L=22 mm into Formula (2)) of the FBG sensor. For this reason, a bandpass filtering process near the primary resonant frequency may be effective to detect an ultrasound response. The related patent application describes that a response waveform is obtained by bandpass filtering with the central frequency 170 kHz. FIG. 11(b) shows the response waveform.

On the other hand, the system proposed by the present embodiment detects the ultrasound clearer than those of (a) and (b) in FIG. 11, though the broadband bandpass filtering process (30 kHz to 500 kHz) is performed on the ultrasound response obtained by the system proposed by the present embodiment.

As obvious from the related patent application and the experiment result of the second embodiment of the present invention, the FBG sensor having a resonant structure shows a response with a high component intensity at the resonant frequency near the frequency of the detected ultrasound. The related patent application (paragraphs 77 and 78) describes that a narrow-band bandpass filtering the output of the opto-electrical converter (the output of the FBG sensor) for each resonant frequency is required for detecting every ultrasound, in the case of using the FBG sensor with a resonant structure. As a result, complex signal processing with multiple narrow-band bandpass filtering is required for the ultrasound response detection without the averaging process based on the technique.

On the other hand, since the optical fiber resonant portion length of the FBG sensor used in the ultrasound detection system based on the present embodiment is 38.5 mm, the resonant frequency increases from 32.9 kHz to 98.6 kHz to 164 kHz to 230 kHz by 66 kHz a degree from the degree 0 in an ascending order of the degree. In the present embodiment, the ultrasound is detected in a highly sensitive manner by bandpass filtering in broadband including the resonant frequencies of the degree 0 to the degree 7. Thereby, the present invention enables a highly sensitive and broadband ultrasound detection. The practical ultrasound/AE detection is significantly improved compared with the related patent application.

The third embodiment describes a case in which the frequency of the detected ultrasound is unknown. If the frequency of the detected ultrasound is known, a highly sensitive ultrasound detection is enabled by frequency filtering for allowing passage of the resonant frequency determined based on the optical fiber resonant portion length between the point in contact with the test object and the free end in the optical fiber to which the FBG is written, in the signal processing such as the filtering process and the amplification process of the electrical signal output from the opto-electrical converter. Further, the resonant frequency can be controlled by adjusting the optical fiber resonant portion length.

(Fourth Embodiment)

A fourth embodiment is an example in which the ultrasound detection system including an FBG sensor with a resonant structure is applied to the AE detection.

Japanese Society for Non-Destructive Inspection standard "Method of measuring degradation of sensitivity of acoustic emission converter" describes a method of correcting the sensitivity of the converter, wherein an elastic wave generated by pressure-breaking a mechanical pencil lead is served as a pseudo AE. In response, an attempt is made to record a response to the pseudo AE that is generated by pressure-braking a mechanical pencil lead on the test object and propagates in the test object, by using the ultrasound detection system based on the present invention.

The ultrasound oscillator of the experiment setup shown in FIG. 9 is removed. A distance between the point at which the FBG sensor is attached to the test object and a point at which the mechanical pencil lead is pressure-broken is set to 250 mm. The FBG sensor has the optical fiber resonant portion length of 38.5 mm. Thus, a response of the FBG to the pseudo AE generated by pressure-breaking the mechanical pencil lead is recorded. An output of the opto-electrical converter that is bandpass filtered with 30 kHz to 1 MHz is used as a trigger signal for recording the response signal. The trigger level is set so that a recording trigger is not set by a background noise in error.

Figure 12:
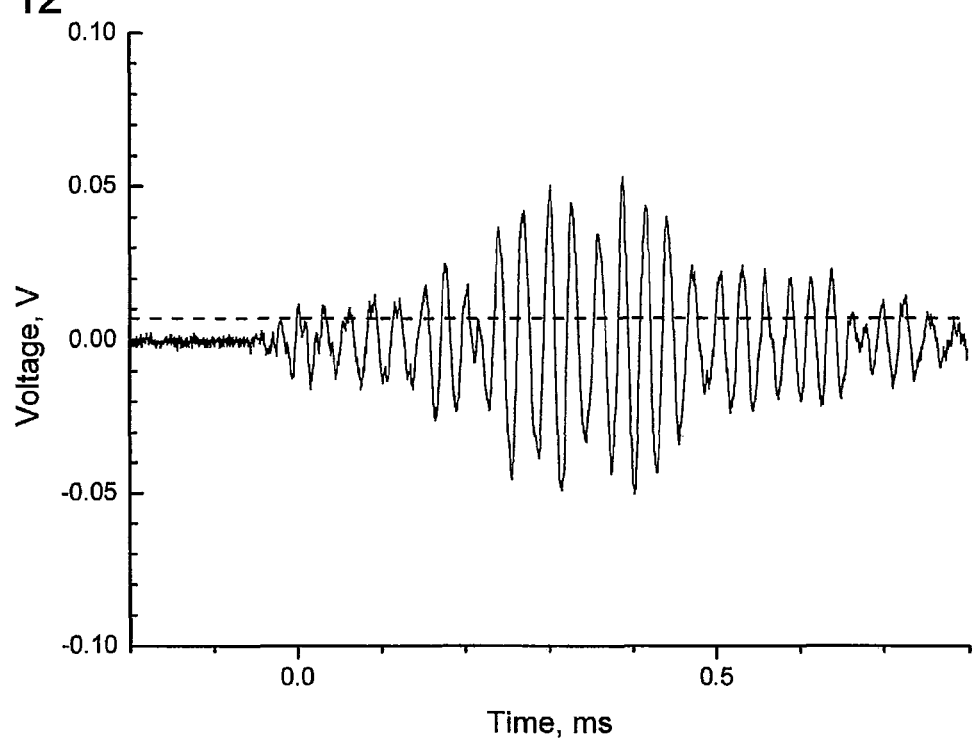
FIG. 12 is a diagram showing a response signal of an FBG sensor with a resonant structure to a pseudo AE generated by pressure-breaking a pencil lead and a trigger level used when the signal is measured and shown by a horizontal dashed line in FIG. 12, in a fourth embodiment.

FIG. 12 shows the response signal to the pseudo AE generated by pressure-breaking the mechanical pencil lead. The trigger level of the measurement is 7 mV and is shown by a horizontal dashed line in FIG. 12. As is seen from FIG. 12, the noise before the pseudo AE is generated is sufficiently smaller than the trigger level. This result shows that the AE can be detected by the system based on the present invention.

(Fifth Embodiment)

Figure 13:
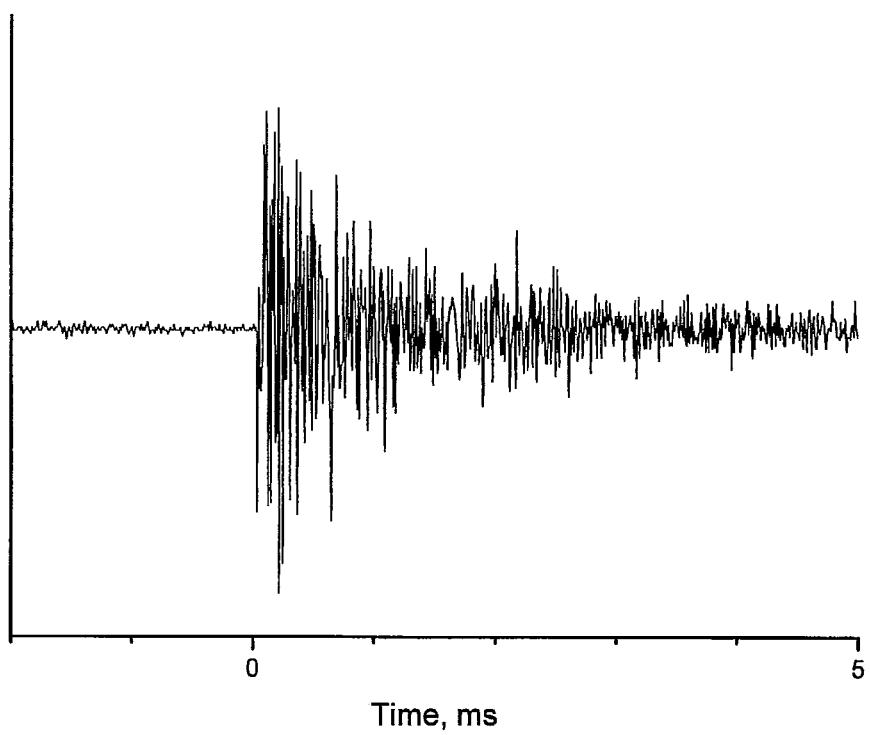
FIG. 13 is a response waveform of an FBG sensor with a non-resonant structure to ultrasound propagating in a material and FIG. 13 is a diagram showing a response waveform on which a bandpass filtering process of 30 kHz to 500 kHz is performed using the system shown in FIG. 9 without performing the averaging process, in a fifth embodiment.

An attempt is made to detect the ultrasound propagating in the test object by using an FBG sensor with a non-resonant structure, in the same experiment as that of the third embodiment, that is, without the averaging process. In the experiment setup used in FIG. 9, the entire FBG is attached to the test object to form an FBG sensor with a non-resonant structure. The distance between the ultrasound oscillator and the optical fiber attached position is set to 150 mm. The ultrasound oscillator with the central frequency 250 kHz is excited by a spike wave. Thus, the ultrasound propagates in the test object. FIG. 13 shows a response waveform of the FBG sensor that is bandpass filtered in 30 kHz to 500 kHz. It can be confirmed that the ultrasound can be detected clearly in the same manner as with a resonant structure. The seventh embodiment of the related patent application describes that the FBG sensor with a non-resonant structure cannot detect an ultrasound propagating in the test object without the averaging process. In contrast, the use of the detection system proposed by the present invention enables detecting ultrasound propagating in the test object, even in an FBG sensor with a non-resonant structure, that is, even when the FBG is directly attached to the test object.

(Sixth Embodiment)

A sixth embodiment is an example in which the ultrasound detection system including an FBG sensor with a non-resonant structure is applied to the AE detection. An attempt is made to carry out the same experiment as that of the fourth embodiment, that is, the measurement of the pseudo AE generated by pressure-breaking a mechanical pencil lead, by using an FBG sensor with a non-resonant structure. In the experiment setup used in the fourth embodiment, the entire FBG is attached to the test object to form an FBG sensor with a non-resonant structure. The distance between the point at which the FBG sensor is attached to the test object and the point at which the mechanical pencil lead is pressure-broken is set to 250 mm. A response of the FBG sensor with a non-resonant structure to the pseudo AE generated by pressure-breaking the mechanical pencil lead is recorded. An output of the opto-electrical converter that is bandpass filtered in 30 kHz to 1 MHz is used as a trigger signal for recording the response signal. The trigger level is set so that a recording trigger is not set by a background noise in error.

Figure 14:
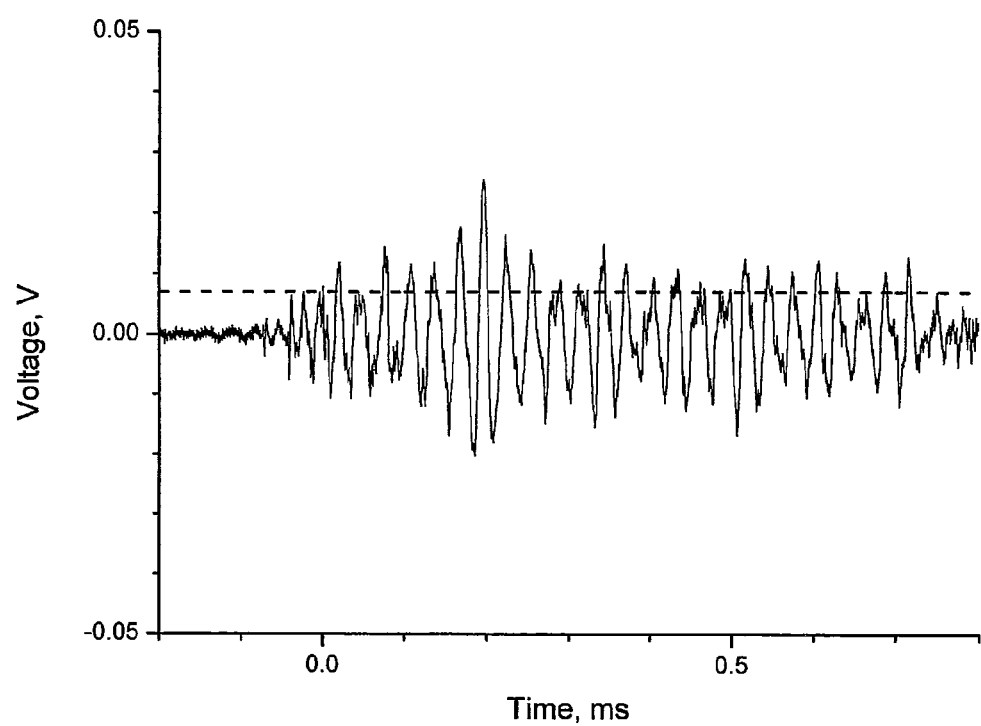
FIG. 14 is a diagram showing a response signal of an FBG sensor with a non-resonant structure to a pseudo AE generated by pressure-breaking a pencil lead and a trigger level used when the signal is measured and shown by a horizontal dashed line in FIG. 14, in a sixth embodiment.

FIG. 14 shows the response signal to the pseudo AE generated by pressure-breaking the mechanical pencil lead. The trigger level of the measurement is 7 mV and is shown by a horizontal dashed line in FIG. 14. As is seen from FIG. 14, the noise before the pseudo AE is generated is sufficiently smaller than the trigger level. This result shows that the AE can be detected by the system based on the present invention, even in use of an FBG sensor with a non-resonant structure.

(Seventh Embodiment)

Figure 15:
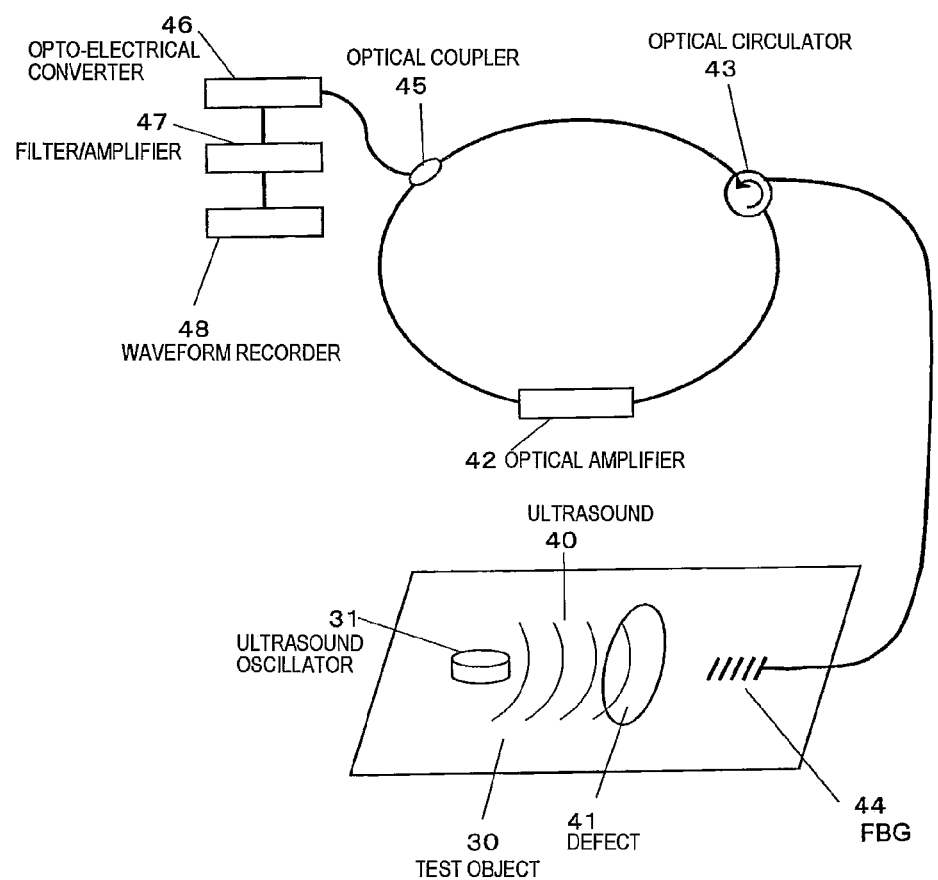
FIG. 15 is a diagram showing ultrasonic defect detection of a seventh embodiment.

Since ultrasound traversing a material is largely scattered and attenuated at a defect portion, the propagation state is different from no defect state. A method for detecting a defect in a material by using the above property is the ultrasonic defect detection. The ultrasound detection system based on the present invention can be used for the ultrasonic defect detection. A seventh embodiment is an example in which the ultrasonic defect detection is performed using the ultrasound detection system of the present invention. FIG. 15 shows an ultrasonic defect detection apparatus of the present embodiment. The ultrasonic defect detection apparatus shown in FIG. 15 includes an optical amplifier 42, an optical circulator 43, an FBG 44, an optical coupler 45, an opto-electrical converter 46, a filter/amplifier 47, and a waveform recorder 48. An optical fiber to which an FBG is written is touched to a test object 30. The ultrasound oscillator 31 is attached onto a line extended in a direction of an optical fiber axis of the FBG 44. Ultrasound 40 oscillated from the ultrasound oscillator 31 is detected by the FBG 44 operating as a sensor.

In the ultrasonic defect detection apparatus shown in FIG. 15, ultrasound traverses a material from the ultrasound oscillator. The ultrasound is detected by the FBG sensor. Thus, the presence or absence of a defect portion between the ultrasound oscillator and the sensor can be detected from the intensity of the response signal and the change of the frequency property. If a defect 41 exists on a line connecting the ultrasound oscillator 31 and the FBG 44, the response signal has decreased intensity compared with the absence of the defect. In addition, different response frequency property appears. Thus, it is possible to determine the presence or absence of the defect.

(Eighth Embodiment)

For the signal processing to detect an ultrasound described in the above embodiments, the following embodiment can be employed. Each embodiment makes the frequency filtering process before the signal is recorded by the waveform recorder, in order to clearly extract the ultrasound/AE response. The extracting the ultrasound/AE response may be made after the signal is recorded, by the same process. In addition to the frequency filtering the sensor output, a spectral subtraction process for removing a background noise component are effective means for detecting the ultrasound/AE and can be provided.

The FBG sensor with a resonant structure outputs a response signal including a large component intensity at the resonant frequency when receiving ultrasound or an AE. Thus, the resonant frequency of the sensor may be set to a measurement signal frequency of a lock-in amplifier and a lock-in amplifier output may be used as a recording trigger, if ultrasound or AE response is recorded by using a resonant type FBG sensor.

The averaging process is effective means for extracting an ultrasound response whether the structure of the FBG sensor is resonant or not. The averaging process can be arbitrarily combined with the filtering processes described in each embodiment.

(Ninth Embodiment)

A ninth embodiment demonstrates a case in which ultrasound is detected while an ultrasound transmitting/receiving point is being moved. The embodiments described above describe a case in which an optical fiber to which an FBG is written is attached to the test object is described. Nevertheless, since many ultrasonic defect detection methods identify the defect position while the ultrasound transmitting/receiving point is being moved, so that it is practical and convenient that both the ultrasound oscillator and the FBG sensor are movable. Patent Document 5 discloses a technique in which the FBG sensor is movable. The sensor unit of the ultrasound detection system based on the present invention may also have the same movable structure as that of the Patent Document 5 such that the FBG sensor is movable.

Figure 16:
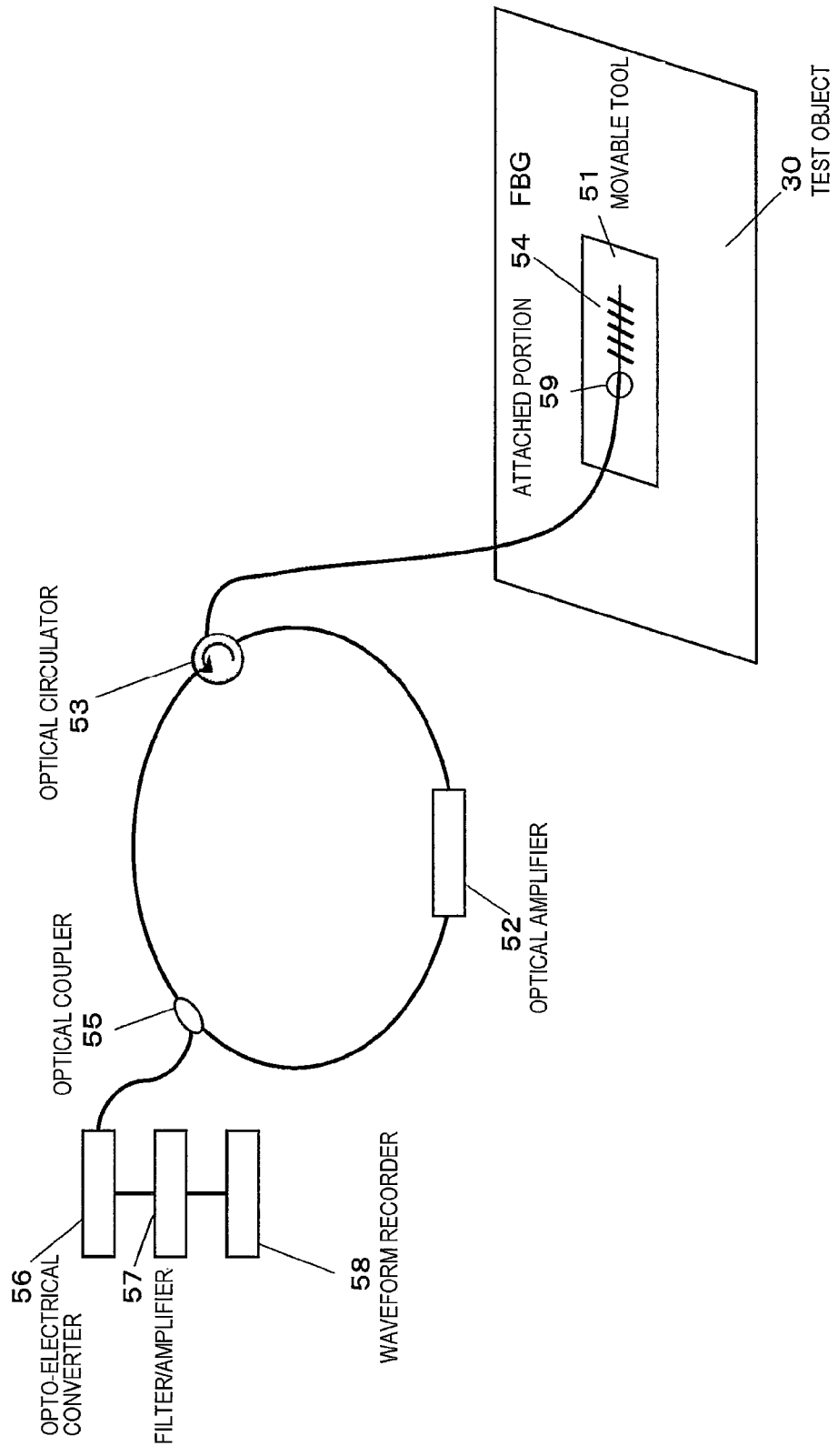
FIG. 16 is a diagram showing an apparatus of a ninth embodiment with a movable sensor unit.

FIG. 16 shows an apparatus in which an ultrasound detection system described in the above embodiments is movable. As shown in FIG. 16, a part of an optical fiber to which an FBG 54 is written is attached to a movable tool 51. Ultrasound transmitted in the test object 30 is transmitted to the optical fiber through the movable tool 51. For example, a part of the FBG 54 of the optical fiber to which the FBG is written or a portion of the optical fiber other than the FBG is touched to a medium where an ultrasound propagation speed is slow or a thin medium having a thickness of 1 mm or less (corresponding to the movable tool 51) at an attached portion 59. In this manner, a movable FBG sensor with resonant property may be formed. The movable FBG sensor is touched to the test object 30. Thus, the ultrasound or the AE propagating in the test object is detected. The apparatus shown in FIG. 16 has the same configuration as that of the system shown in FIG. 9 except for the movable structure. The apparatus includes an optical amplifier 52, an optical circulator 53, an optical coupler 55, an opto-electrical converter 56, a filter/amplifier 57, and a waveform recorder 58.

FIG. 16 illustrates an example of the resonant type FBG sensor. Instead, a non-resonant structure FBG sensor may be attached to a movable tool. Thus, a movable vibration detection system is formed. Specifically, the ultrasound or the AE propagating in the test object is detected as follows: a movable FBG sensor is formed by bringing an FBG into contact a medium where an ultrasound propagation speed is slower than that in the test object or a thin medium having a thickness of 1 mm or less; the movable FBG sensor is brought into contact with the test object.

Since the FBG sensor is formed to be movable, the ultrasound detection and the ultrasonic defect detection test can be easily performed.

(Tenth Embodiment)

The present embodiment describes a case in which the embodiments described above are applied and extended to a system including a plurality of FBGs.

Figure 17:
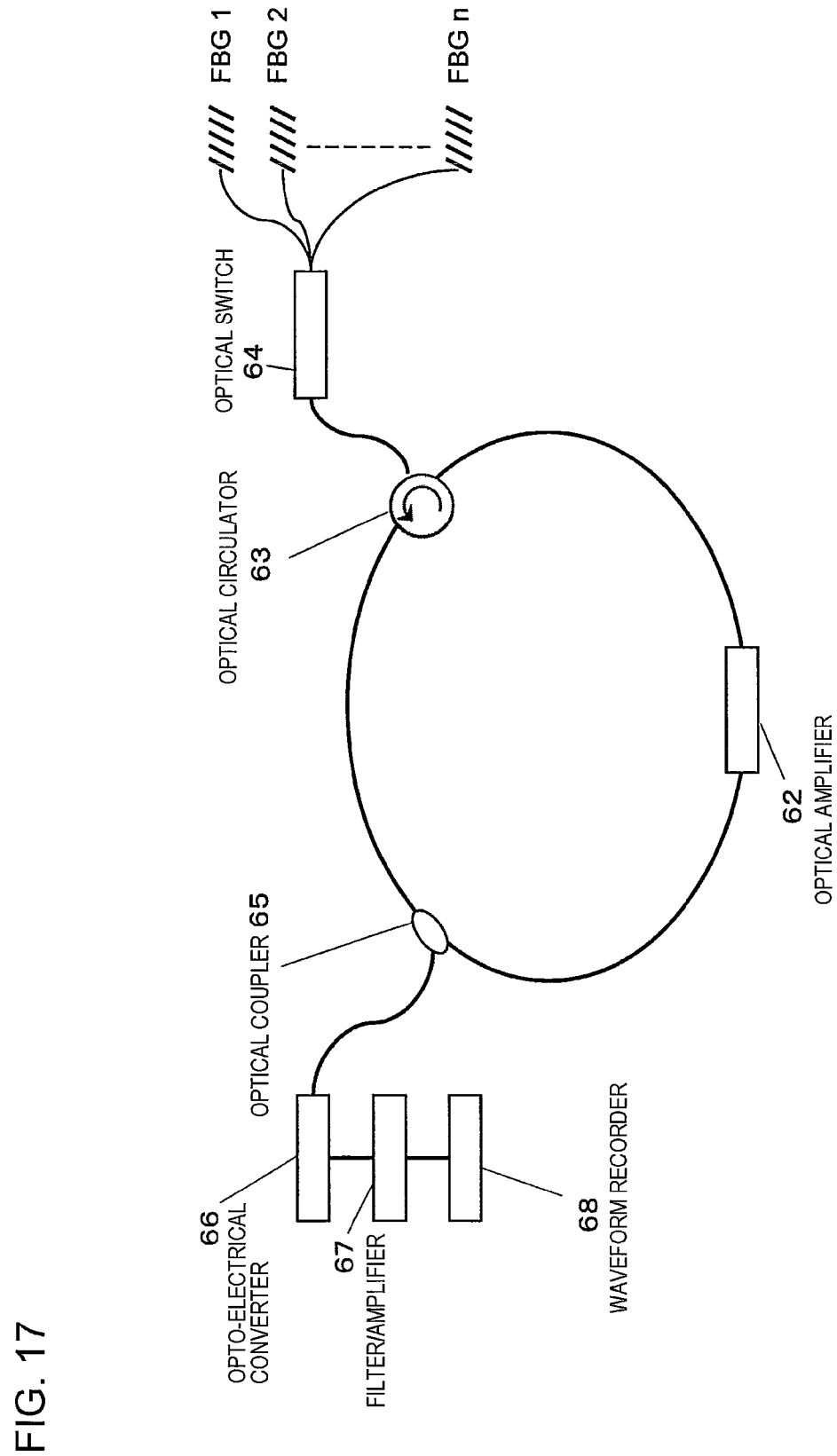
FIG. 17 is a diagram showing a multi-point measurement apparatus that uses an optical switch in a tenth embodiment.

FIG. 17 shows an apparatus for performing a multi-point measurement by using an ultrasound detection system of the present invention. The multi-point measurement apparatus shown in FIG. 17 includes an optical amplifier 62, an optical circulator 63, an optical coupler 65, a plurality of FBGs (1, 2, . . . , n), an opto-electrical converter 66, a waveform recorder 68, and an optical switch 64. A filter/amplifier 67 is provided as needed. One of the FBGs (1, 2, . . . , n) lasing reflection light by the optical amplifier 62 is selected by using the optical switch 64.

Figure 18:
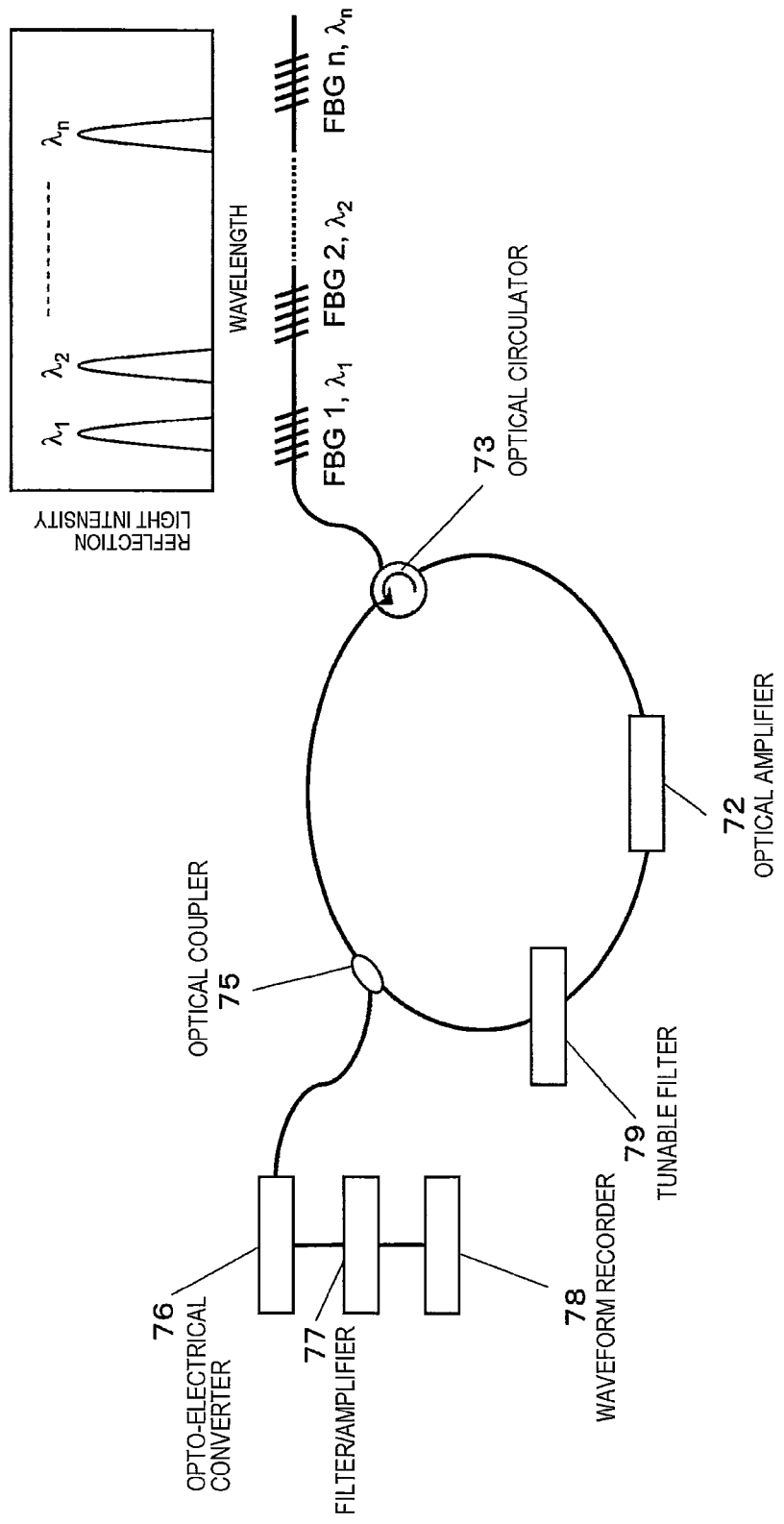
FIG. 18 is a diagram showing a multi-point measurement apparatus that uses a tunable filter in the tenth embodiment.

FIG. 18 shows an apparatus for performing a multi-point measurement by using an ultrasound detection system of the present invention. The multi-point measurement apparatus shown in FIG. 18 includes an optical amplifier 72, an optical circulator 73, an optical coupler 75, a plurality of FBGs (1, 2, . . . , n), an opto-electrical converter 76, a waveform recorder 78, and a tunable filter 79. A filter/amplifier 77 is provided as needed. When the tunable filter 79 has property to transmit a reflection spectrum of any one of FBGs, one of the FBGs lasing reflection light by the optical amplifier 72 can be selected by using the tunable filter. The same capability is made also when the tunable filter is disposed between the optical coupler and the opto-electrical converter in FIG. 18 or between the optical circulator and the FBG sensor.

Figure 19:
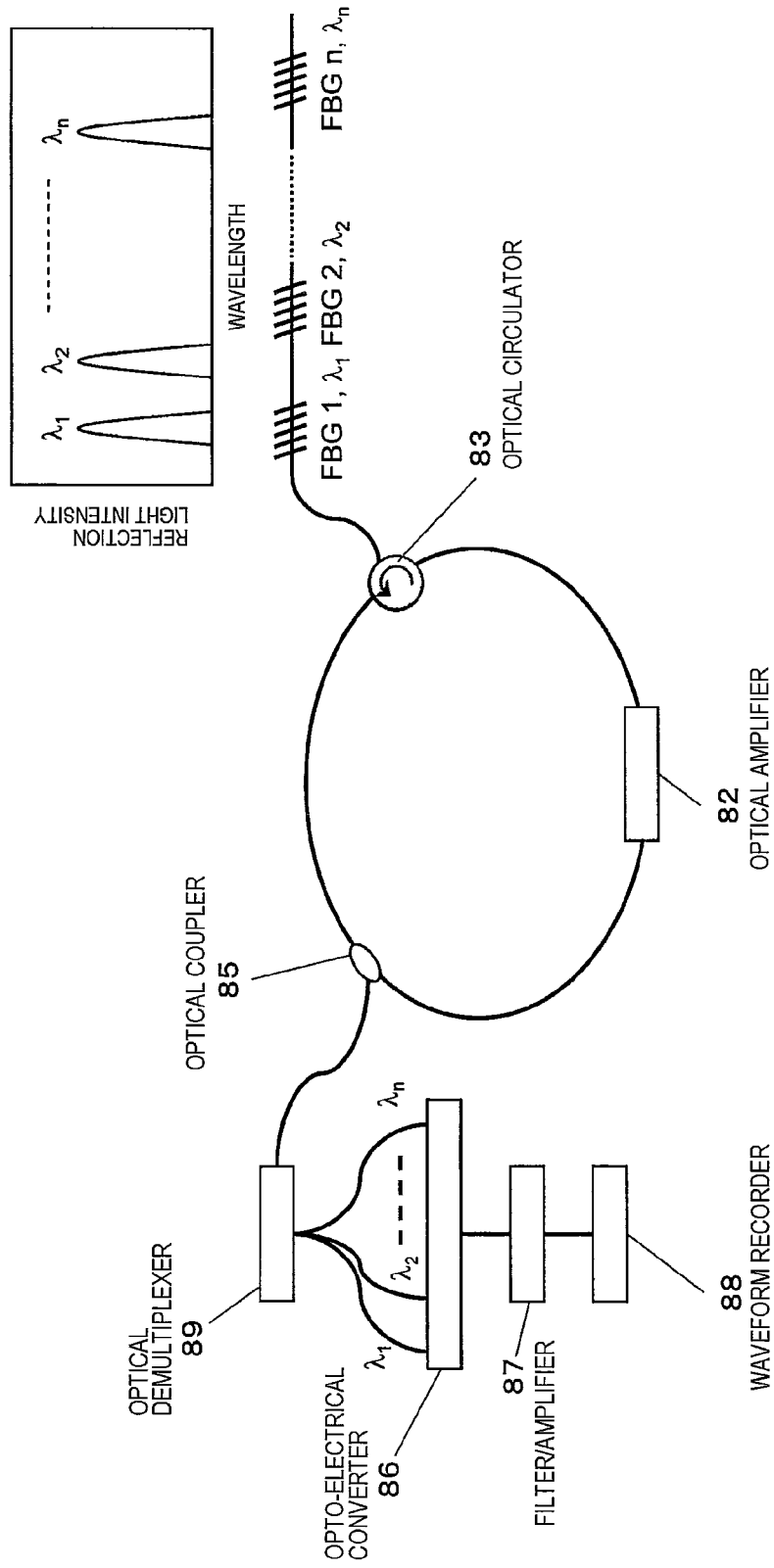
FIG. 19 is a diagram showing a simultaneous multi-point measurement apparatus that uses a wavelength separation technique in the tenth embodiment.

FIG. 19 shows an apparatus for performing a simultaneous multi-point measurement by using an ultrasound detection system of the present invention. The simultaneous multi-point measurement apparatus shown in FIG. 19 includes an optical amplifier 82, an optical circulator 83, an optical coupler 85, a plurality of FBGs (1, 2, . . . , n), an opto-electrical converter 86, a waveform recorder 88, and an optical demultiplexer 89. A filter/amplifier 87 is provided as needed. The simultaneous multi-point measurement apparatus shown in FIG. 19 simultaneously measures a plurality of lased FBG reflection intensities, as follow: lased reflection light from a plurality of FBGs with different Bragg wavelengths is allowed to pass through the optical demultiplexer 89 with different output lines depending on the wavelength; the lased reflection light intensities from the FBGs are output to different lines ($\lambda_1, \lambda_2, \ldots, \lambda_n$); and the lased reflection light intensities from the FBGs are measured. The example illustrated in FIG. 19 limits the number of the optical fibers in the FBG sensors to one. Instead, a sensor network composed of a plurality of the optical fibers provided with the FBG sensors may be formed by connecting 1×N optical switches or 1×N optical couplers to the entry/exit port of the optical circulator.

(Eleventh Embodiment)

The detection of impact load is an important technique not only for the soundness evaluation of a structure, but also for anti-crime/anti-disaster detection. An eleventh embodiment is an example in which the present invention is applied to an anti-crime/anti-disaster detection apparatus. An experiment will be described in which an impact load is detected by using an vibration detection system proposed by the present invention. In the experiment setup shown in FIG. 9, the ultrasound oscillator is removed. Then, an attempt is made to detect an impact vibration caused by dropping a ceramic ball having a weight of 2.7 g from the height of 30 mm to the surface of the test object 150 mm apart from the FBG sensor, by the FBG sensor with a non-resonant structure and the FBG sensor with a resonant structure.

Figure 20:
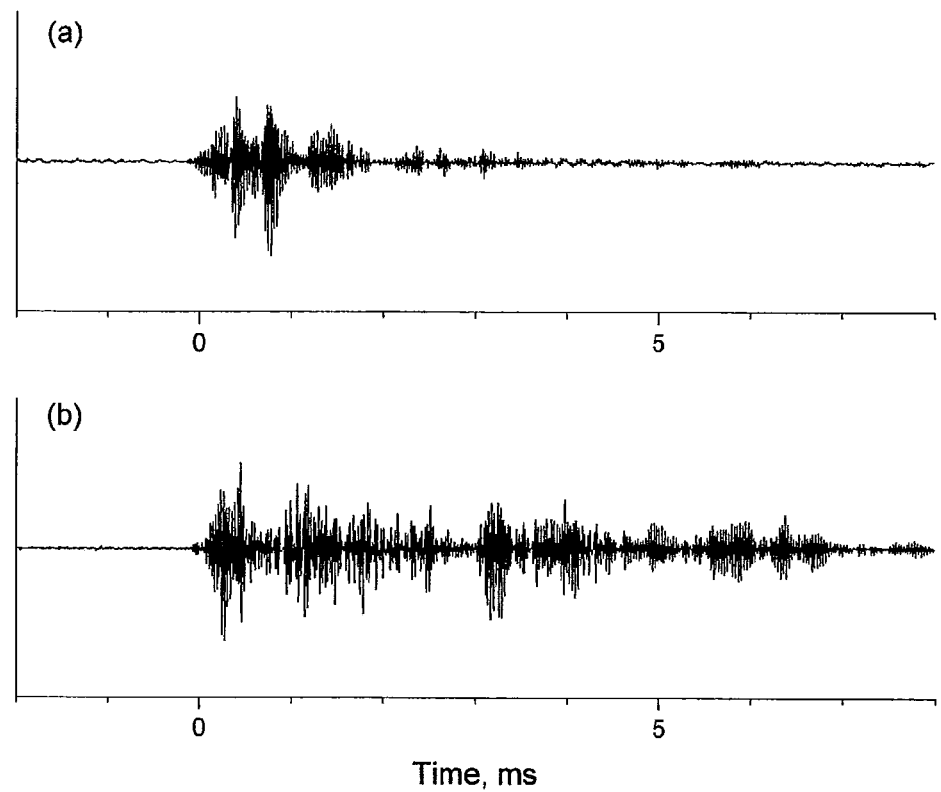
FIG. 20 is a diagram showing response signals of an FBG sensor when a falling ball impact is applied to a flat plate in an eleventh embodiment.

In FIG. 20, (a) shows a falling ball impact response waveform detected by the FBG sensor with a non-resonant structure and (b) shows a falling ball impact response waveform detected by the FBG sensor with a resonant structure having the optical fiber resonant portion length of 38.5 mm. In the measurement of the response waveform, the filter is set to a high-pass filter with the cut-off frequency 30 kHz. The above waveform recording performs the 30 kHz high pass filtering process to remove background noise. Nevertheless, it is confirmed that no filtering process is required when an impact load is detected, because the response signal intensity in impact is significantly larger than the background noise level. In a resonant structure, the impact vibration flowing into the optical fiber resonant portion propagates bi-directionally. For this reason, the response duration time is longer than that of a sensor with a non-resonant structure. In any way, it is shown that the falling ball impact is detected in a highly sensitive manner regardless of the presence or absence of the resonant structure of the FBG sensor.

In this way, it is possible to detect generation of an impact load from the FBG sensor by using the vibration detection system based on the present invention. Accordingly, it is also possible to determine the impact position by arranging a plurality of FBG sensors on the test object using the tenth embodiment and calculating from the differences between the detection times of the impact load detected by the FBG sensors. The detection of the impact load and the determination of the impact load position can be applied to a detection apparatus and an alarm apparatus in anti-crime or anti-disaster technique.

(Twelfth Embodiment)

A twelfth embodiment is an example in which the vibration detection system of the present invention is applied to a vibration detection of vibration of a frequency lower than or equal to the ultrasound band, that is, a frequency lower than or equal to 20 kHz. An experiment example in application of detecting vibration lower than or equal to 20 kHz will be described. In the system shown in FIG. 9, the ultrasound oscillator is removed and one end of the test object is fixed by a fixing tool such as a vice. Thus, a cantilever structure is formed. The FBG sensor has a non-resonant structure in which the entire length of the FBG is attached to the test object. To measure a strain, a resistance type strain gauge is attached near the FBG. When a free oscillation is applied to the test object with a cantilever structure, a low pass filtering process with cut-off frequency of 100 kHz is performed on the output of the FBG sensor and the output of the strain gauge and the outputs are recorded.

Figure 21:
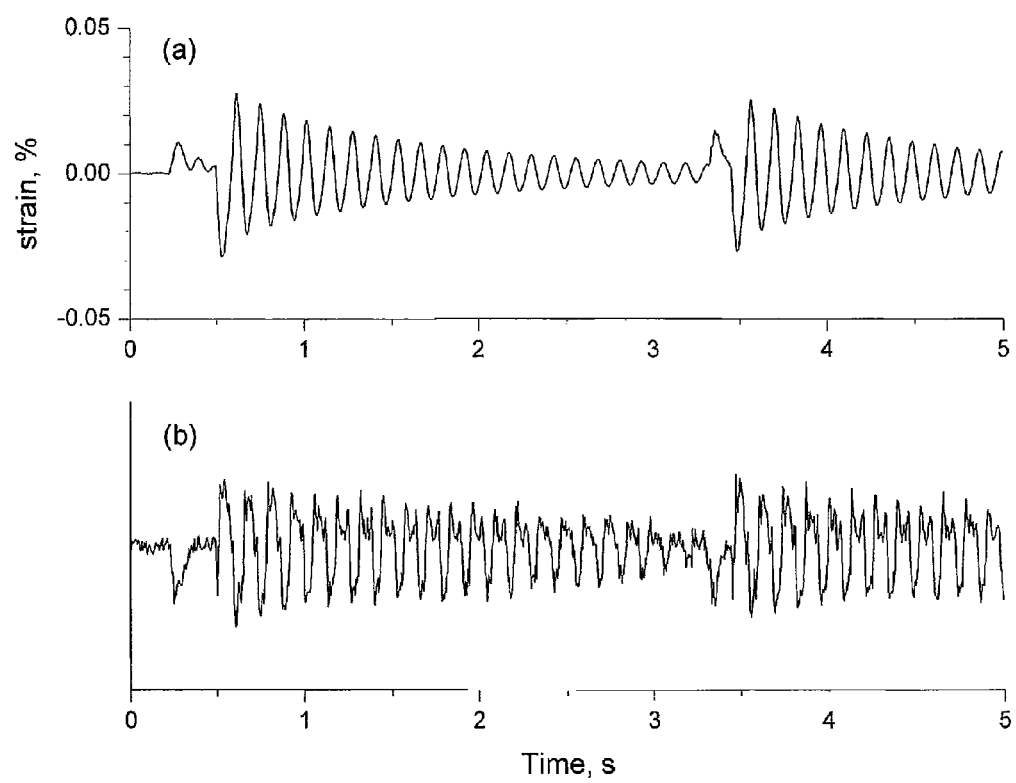
FIG. 21 is diagrams when a free oscillation is applied to a cantilever beam.

FIG. 21(a) shows a strain variation measured by the strain gauge and FIG. 21(b) shows an FBG sensor response when the free oscillation is applied to the cantilever. As is seen from the strain variation in FIG. 21(a), the cantilever is bent at time about 0.2 s and the bending load is released at time about 0.5 s in this test. Thus, the cantilever oscillates freely. Thereafter, the cantilever is bent again at test time about 3.2 s. The vibration frequency of the cantilever at this time is about 7.5 Hz. The output of the FBG sensor shown in FIG. 21(b) has a reverse phase of the phase of the output of the strain gauge. Anyway, it is seen that the output of the FBG sensor shows the same signal variation as the strain variation evaluated from the strain gauge. In this way, it is possible to detect vibration of Hz order from the FBG sensor by using the vibration detection system of the present invention. For this reason, it is possible to detect a low frequency vibration of sub-Hz order, which is lower than 1 Hz.

(Thirteenth Embodiment)

Figure 22:
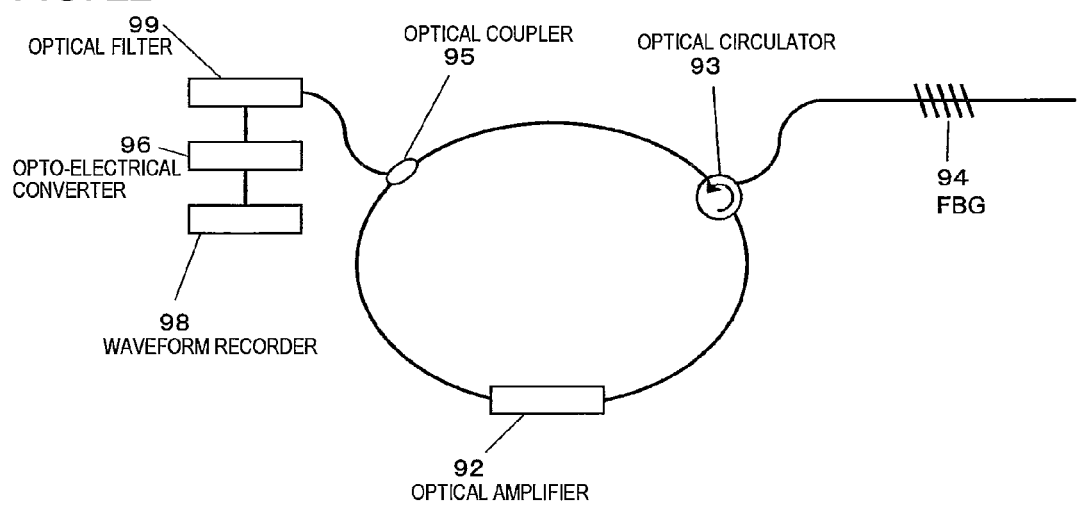
FIG. 22 is a diagram showing an apparatus of a thirteenth embodiment, in which a fiber laser, as a light source, is combined with a system that uses an optical filter to demodulate a signal.

A thirteenth embodiment is an example in which a fiber laser is used as a light source and combined with a demodulation optical filter. FIG. 22 shows an apparatus in which a fiber laser is combined as a light source in a system using an optical filter to demodulate a signal. The ultrasound measurement system in FIG. 22 includes an optical amplifier 92, an optical circulator 93, an FBG 94, an optical coupler 95, an optical filter 99, an opto-electrical converter 96, and a waveform recorder 98. The FBG reflection light is incident on the optical filter through the optical coupler 95.

As shown in FIG. 4, the reflection spectrum of the FBG has narrower band and higher intensity compared with a case of using a broadband light source, if a fiber laser, characterizing the present invention, is used as a light source. A conventional technique may be employed for a structure related to the demodulation optical filter. Non-Patent Document 1 describes an example in which many of ultrasound detection systems that use a conventional broadband light source enters the reflection light from the FBG sensor to the optical filter and use a phenomenon that the intensity variation of the reflection light or the transmission light of the filter correspond to the ultrasound vibration received by the FBG.

If a fiber laser is used as a light source as in the present embodiment, a narrow band and high intensity FBG reflection spectrum is obtained. As a result, it is possible to perform much more sensitive vibration detection than using a broadband light source.

(Fourteenth Embodiment)

Figure 23:
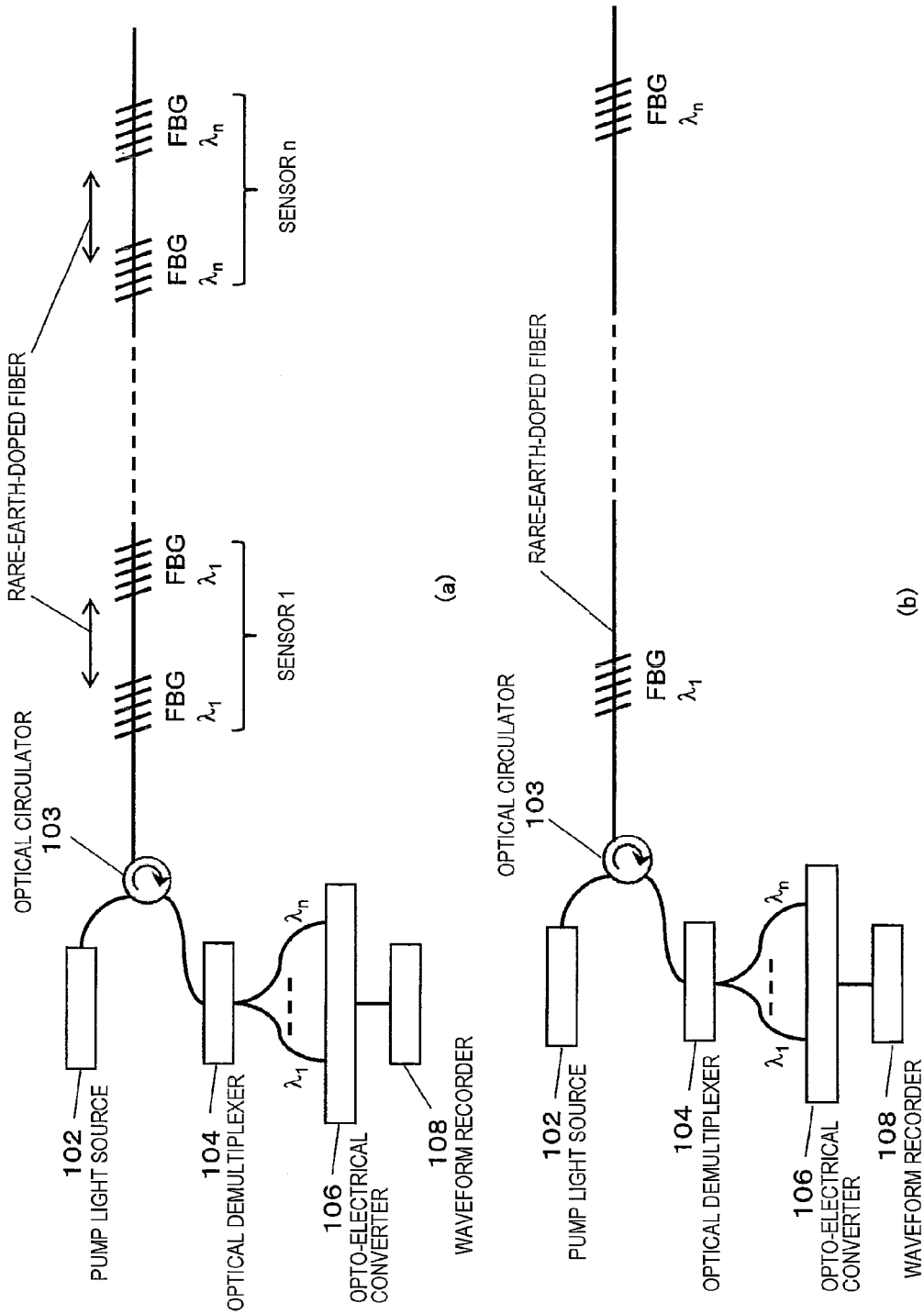
FIG. 23 is a diagram showing an example of a configuration of a system that uses a grating type fiber laser in a fourteenth embodiment.

The present embodiment is an example in which a resonator structure of the fiber laser, which is different from that in the first embodiment, is used. The fiber laser resonator structure is categorized into two types containing an FBG type that forms an FBG at both ends of the resonator and a ring type that forms a ring-shaped resonator. FIG. 23 shows an ultrasound measurement system using the FBG type resonator structure that forms an FBG at both ends of the resonator. The first to the thirteenth embodiments describe only a ring type fiber laser. Even when an FBG type fiber laser as shown in (a) and (b) in FIG. 23 is used, the above embodiments can be realized.

The ultrasound measurement system in FIG. 23(a) includes a pump light source 102, an optical circulator 103, an FBG sensor 1 to an FBG sensor n, an optical demultiplexer 104, an opto-electrical converter 106, and a waveform recorder 108. Each of the FBG sensor 1 to the FBG sensor n includes two FBGs having the same Bragg wavelength. As shown in FIG. 23(a), an amplifying medium is inserted between FBGs having the same Bragg wavelength. In this case, it is possible to obtain reflection light lasing at the Bragg wavelength. For example, when a rare-earth-doped fiber is used as the amplifying medium, lased FBG reflection light can be obtained by entering pump light to a fiber to which an FBG is written. In this case, the two FBGs having the same Bragg wavelength functions as one sensor. As shown in FIG. 23(a), a plurality of sensors can be arranged on one fiber.

FIG. 23(b) is an example in which FBGs are written to a rare-earth-doped fiber having an amplification function. In the same manner as in FIG. 23(a), the ultrasound measurement system in FIG. 23(b) includes a pump light source 102, an optical circulator 103, FBG ($\lambda_1$) to FBG ($\lambda_2$), an optical demultiplexer 104, an opto-electrical converter 106, and a waveform recorder 108. Each FBG can have a function as a sensor. The multiplexing is easy as shown in FIG. 23(b).

FIG. 23 demonstrates an FBG type fiber laser using rare-earth-doped fiber amplification. Even when fiber Raman amplification is used, the same effect can be obtained.

(Fifteenth Embodiment)

The present embodiment is an example in which a fiber laser is used as a light source. Strain and temperature received by the test object are measured.

Laser light having the Bragg wavelength of FBG at a lasing wavelength can be obtained by the fiber laser. Since the Bragg wavelength of the FBG varies in proportion to strain and temperature, the strain and temperature received by the test object can be measured from the variation of the Bragg wavelength, by attaching the FBG to the test object or burying the FBG in the test object. Examples of a method for quantitatively measuring the Bragg wavelength of the FBG include a method that uses measurement equipment such as an optical spectrum analyzer or a wavelength meter and a method for converting a wavelength change into a light intensity change by using an optical filter whose transmission property varies according to wavelength. Details of the Bragg wavelength measurement method using an optical filter is described in Non-Patent Document 2.

Figure 24:
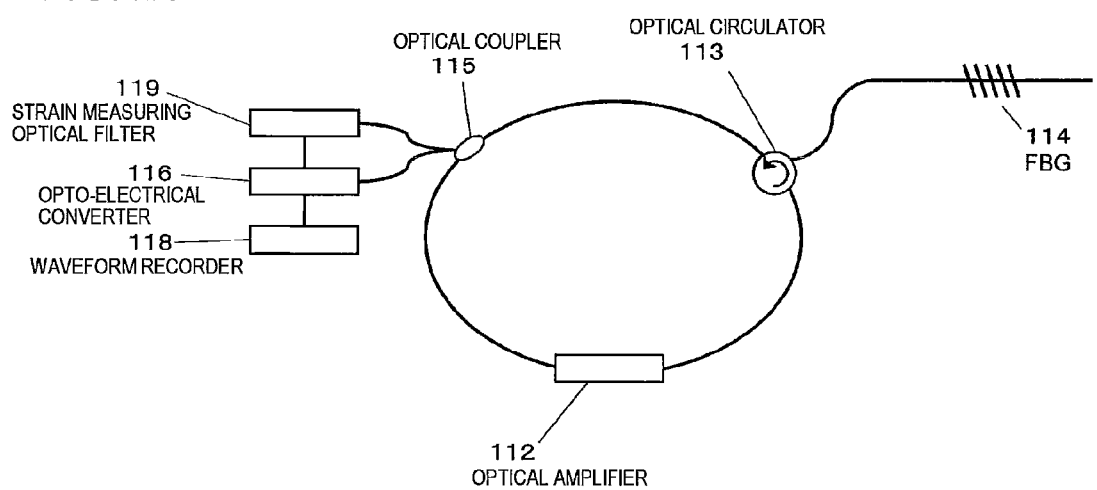
FIG. 24 is a diagram showing a configuration of a system that measures ultrasound, strain, and temperature at the same time in a fifteenth embodiment.
Figure 25:
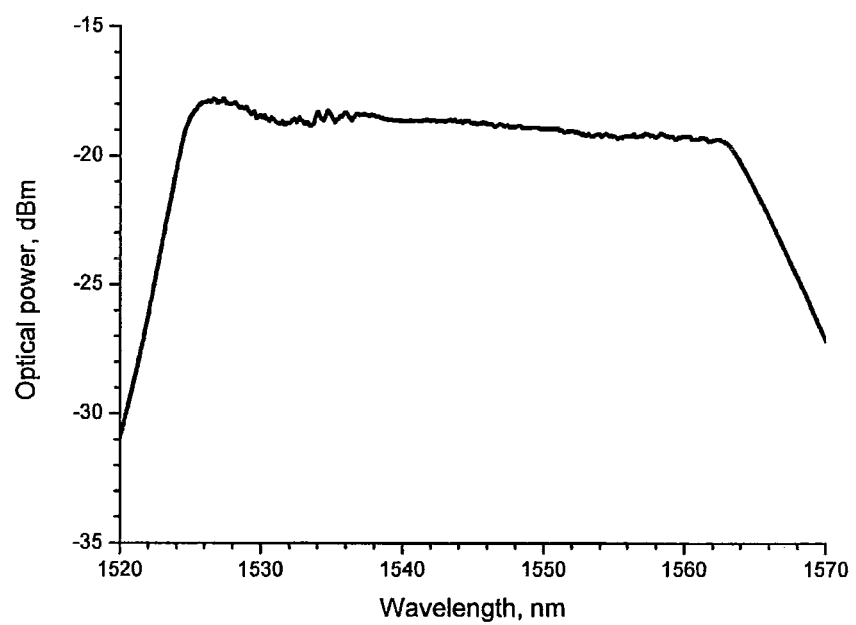
FIG. 25 is a diagram showing light output wavelength dependence of a broadband light source used in an experiment described in the related patent application.
Figure 26:
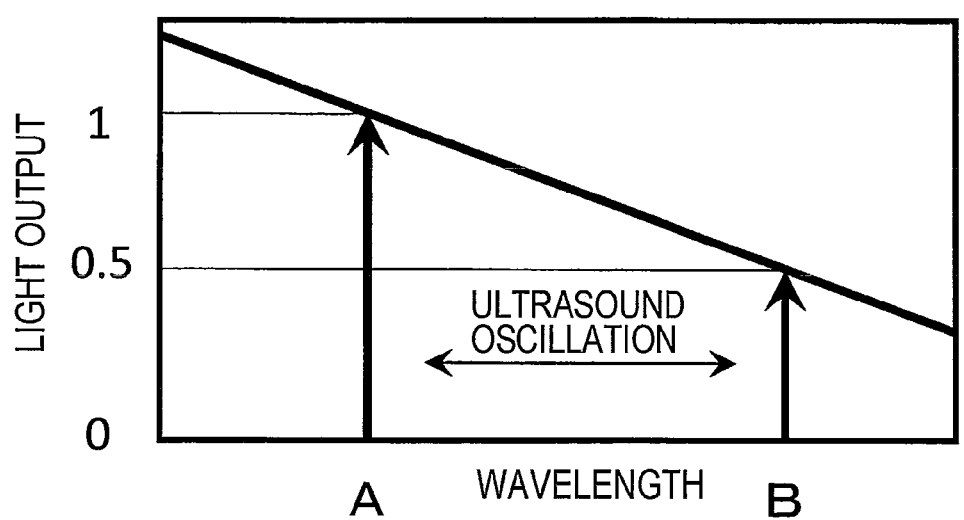
FIG. 26 is a diagram showing wavelength dependence of light output.

The present embodiment will be described with reference to FIG. 24. FIG. 24 shows a configuration of a system that measures ultrasound, strain, and temperature at the same time. The system in FIG. 24 includes an optical amplifier 112, an optical circulator 113, an FBG 114, an optical coupler 115, a strain measuring optical filter 119, an opto-electrical converter 116, and a waveform recorder 118. As shown in FIG. 24, the lased FBG reflection light is extracted from the optical coupler 115 for detecting ultrasound, while the lased FBG reflection light is put into the optical filter 119 whose transmission property varies over broadband according to wavelength, for measuring the strain and temperature. The light transmitted through the optical filter and the reflection light output are put into the opto-electrical converter. The Bragg wavelength can be uniquely evaluated from the opto-electrical converter output through the optical filter 119 and the strain. The temperature received by the test object can be quantitatively evaluated. This system enables quantitatively evaluating not only the ultrasound and the AE, but also the strain and the temperature received by the test object at the same time. Even when the optical filter in FIG. 24 is replaced by an optical spectrum analyzer or a wavelength meter, the same function can be obtained.

The ultrasound detection system of the present invention can be applied to apparatuses for defect detection by the ultrasonic defect detection, defect occurrence detection by the AE detection, machine failure occurrence detection by the vibration detection, determination of the impact load position, anti-crime/anti-disaster detection, and strain and temperature measurement, which are described in the embodiments.

In the present invention, the signal processing described in each embodiment can be arbitrarily combined and performed. The examples shown in the above embodiments are described to facilitate understanding of the invention, and the invention is not limited to the embodiments.

Industrial Applicability

The present invention is effective for defect detection by the ultrasonic defect detection, defect occurrence detection by the AE detection, machine failure occurrence detection by the vibration detection, anti-crime/anti-disaster detection, and the like.

Reference Signs List

1, 11, 21, 31 Ultrasound oscillator
2 Broadband light source
3, 13, 23, 33, 43, 53, 63, 73, 83, 93, 103, 113 Optical circulator
4, 14, 24, 34, 44, 54, 94, 114 FBG
5, 16, 26, 36, 46, 56, 66, 76, 86, 96, 106, 116 Opto-electrical converter
6 Amplifier
7 Filter
8, 18, 28, 38, 48, 58, 68, 78, 88, 98, 108, 118 Waveform recorder
9, 19, 29, 39, 59 Attached portion
12, 22, 32, 42, 52, 62, 72, 82, 92, 112 Optical amplifier
15, 25, 35, 45, 55, 65, 75, 85, 95, 115 Optical coupler
17, 27, 37, 47, 57, 67, 77, 87 Filter/amplifier
30 Test object
40 Ultrasound
41 Defect
51 Movable tool
64 Optical switch
79 Tunable filter
89, 104 Optical demultiplexer
99 Optical filter
102 Pump light source
119 Strain measuring optical filter

The invention claimed is:

1. A vibration detection system for detecting vibration, the system comprising:
    a fiber laser including:
        a Fiber Bragg Grating (FBG) operating as a reflection mirror of the fiber laser, such that the fiber laser has a resonant structure, and
        an opto-electrical conversion unit converting intensity of reflection light from the FBG into an electrical signal, the reflection light being lased by the fiber laser;
    an optical amplifier;
    an optical circulator; and
    an optical coupler,
    wherein the fiber laser has a lasing wavelength at the Bragg wavelength of the FBG, the Bragg wavelength being determined by the optical amplifier configured for optical amplification in a wavelength range that comprises a reflection wavelength of the FBG by using the FBG for a sensor operating as a reflection mirror.

2. The vibration detection system according to claim 1, wherein
    the FBG and an entry/exit port of the optical circulator are connected by an optical fiber,
    the optical coupler and the optical amplifier are inserted between an entry port and an exit port of the optical circulator, and
    the entry port and the exit port are connected by an optical fiber.

3. The vibration detection system according to claim 2, wherein
    reflection light from the FBG traverses a ring-shaped optical fiber through the optical circulator, wherein the optical coupler and the optical amplifier are inserted into the ring-shaped optical fiber,
    the reflection light is amplified by the optical amplifier, incident on the FBG through the optical circulator, and reflected again by the FBG, and
    amplification of the FBG reflection light is repeated in an optical fiber ring-shaped portion in which the optical amplifier is inserted, thereby generating a laser having a lasing wavelength at the Bragg wavelength of the FBG.

4. The vibration detection system according to claim 1, wherein
    an FBG sensor is allowed to have resonant property by contact of a test object with a part of the FBG of an optical fiber to which the FBG is written or a portion of the optical fiber other than the FBG, and
    vibration is transmitted to the optical fiber through a portion in contact with the test object.

5. The vibration detection system according to claim 1, further comprising an optical filter.

6. The vibration detection system according to claim 1, further comprising a signal processing unit, the signal processing unit frequency filtering the electrical signal.

7. The vibration detection system according to claim 6, wherein the frequency filtering is bandpass filtering near a resonant frequency band based on resonant property.

8. The vibration detection system according to claim 1, further comprising a plurality of the FBGs, wherein a multipoint measurement is performed.

9. The vibration detection system according to claim 1, wherein the FBG is a movable FBG sensor and the movable FBG sensor is in contact with a test object.

10. The vibration detection system according to claim 1, wherein the vibration is a vibration of a frequency lower than or equal to 20 kHz including vibration of sub-Hz, an ultrasound, or an acoustic emission.

11. The vibration detection system according to claim 1, wherein the vibration is detected while strain and temperature are measured by using FBG reflection light lased by the fiber laser.

12. An ultrasonic defect detection apparatus comprising the vibration detection system according to claim 1.

13. A material soundness evaluation apparatus that evaluates soundness of a test object by measuring an ultrasound propagation state using the vibration detection system according to claim 1.

14. A material soundness evaluation apparatus that evaluates soundness of a test object by detecting an acoustic emission generated when a material is broken using the vibration detection system according to claim 1.

15. An anti-crime anti-disaster apparatus that detects an impact load by using the vibration detection system according to claim 1.

16. An anti-crime anti-disaster apparatus that detects an impact load and determines an impact position by using the vibration detection system according to claim 1.

17. A failure detection apparatus that detects a vibration by using the vibration detection system of claim 1 and diagnoses a failure of a machine from a vibration state.

18. A vibration detection method comprising:
operating an FBG as a reflection mirror of a fiber laser, such that the fiber laser has a resonant structure, in a system including an optical circulator and an optical coupler; and
detecting a vibration by converting intensity of light reflected from the FBG into an electrical signal, the reflected light being lased by the fiber laser,
wherein the fiber laser has a lasing wavelength at the Bragg wavelength of the FBG, the Bragg wavelength being determined by the optical amplifier configured for optical amplification in a wavelength range that comprises a reflection wavelength of the FBG by using the FBG for a sensor operating as a reflection mirror.

* * * * *